United States Patent
Deng

(10) Patent No.: US 11,648,221 B2
(45) Date of Patent: May 16, 2023

(54) KRAS AGONISTS, PHARMACEUTICAL COMPOSITIONS, AND USES IN MANAGING CANCER

(71) Applicant: Emory University, Atlanta, GA (US)

(72) Inventor: Xingming Deng, Atlanta, GA (US)

(73) Assignee: Emory University, Atlanta, GA (US)

( * ) Notice: Subject to any disclaimer, the term of this patent is extended or adjusted under 35 U.S.C. 154(b) by 220 days.

(21) Appl. No.: 17/034,908

(22) Filed: Sep. 28, 2020

(65) Prior Publication Data

US 2021/0093597 A1 Apr. 1, 2021

Related U.S. Application Data

(60) Provisional application No. 62/907,188, filed on Sep. 27, 2019.

(51) Int. Cl.
*A61K 31/195* (2006.01)
*A61P 35/00* (2006.01)
*A61K 45/06* (2006.01)

(52) U.S. Cl.
CPC ............ *A61K 31/195* (2013.01); *A61K 45/06* (2013.01); *A61P 35/00* (2018.01)

(58) Field of Classification Search
CPC .............................. A61K 31/165; A61P 35/00
See application file for complete search history.

(56) References Cited

FOREIGN PATENT DOCUMENTS

WO    WO-2018144869 A1 *    8/2018

OTHER PUBLICATIONS

Deer (Pancreas vol. 39 pp. 425-435 published 2010) (Year: 2010).*
Caiola (Journal of Experimental and Clinical Cancer Research vol. 37 pp. 302 (2018), (Year: 2018).*
Baker et al ., Journal of Pharmaceutical Science vol. 56 pp. 38-42 published 1967. (Year: 1967).*
Baker (J. Pharmaceutical Sciences vol. 56 pp. 38-42 published 1967). (Year: 1967).*
Baker et al. Irreversible Enzyme Inhibitors. LXXII. Candidate Active-Site-Directed Irreversible Inhibitors of Dihydrofolic Reductase. VI. Derivatives of Hydrophobically Bonded P-Alkyl and P-Aralkyl Benzoic Acids, Journal of pharmaceutical sciences, 1967, 56(1):38-42.
Cox et al. Drugging the undruggable RAS: Mission Possible? Nat Rev Drug Discov, 2014, 13(11):828-51.
Lagoutte et al. Covalent inhibitors: an opportunity for rational target selectivity, Current Opinion in Chemical Biology 2017, 39:54 63.
Lito et al. Allele-specific inhibitors inactivate mutant KRAS G12C by a trapping mechanism, Science, 2016, 351(6273): 604-608.
Liu et al. Targeting the untargetable KRAS in cancer therapy, Acta Pharmaceutica Sinica B 2019;9(5):871-879.
Mai et al. A treatment strategy for KRAS-driven tumors, Nature Medicine, 2018, vol. 24, 899-907.
Ostrem et al. K-Ras(G12C) inhibitors allosterically control GTP affinity and effector interactions, Nature, 2013, 503(7477):548-51.
Overmeyer et al. Death Pathways Triggered by Activated Ras in Cancer Cells, Front Biosci, 2011, 16: 1693-1713.
Patricelli et al. Selective Inhibition of Oncogenic KRAS Output with Small Molecules Targeting the Inactive State, Cancer Discov; 6(3); 316-29, 2016.
Peeters et al. Fructose-1,6-bisphosphate couples glycolytic flux to activation of Ras, Nat Commun, 2017, 8(1):922.
PubChem, Compound CID 270269, 4-{4-[(Bromoacetyl)amino]butyl}benzoic acid, available at https://pubchem.ncbi.nlm.nih.gov/compound/270269.
Welsch et al. Multivalent small molecule pan-RAS inhibitors, Cell, 2017, 168(5): 878-889.e29.
Xu et al. Small Molecule KRAS Agonist for Mutant KRAS Cancer Therapy, Molecular Cancer (2019) 18:85.
Xu et al. Correction to: Small Molecule KRAS Agonist for Mutant KRAS Cancer Therapy, 2020 to Mol Cancer (2019) 18:85.

* cited by examiner

*Primary Examiner* — Theodore R. Howell
*Assistant Examiner* — George W Kosturko
(74) *Attorney, Agent, or Firm* — Emory Patent Group

(57) ABSTRACT

In certain embodiments, this disclosure relates to KRAS agonists, pharmaceutical composition, and uses in managing cancer. In certain embodiments, the KRAS agonist is 4-(4-(2-bromoacetamido)butyl)benzoic acid, salt, prodrug, or derivative thereof. In certain embodiments, this disclosure relates to methods of treating cancer comprising administering an effective amount of a compound of Formula I,

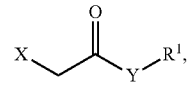

Formula I salt, prodrug, or derivative thereof, to a subject in need thereof, wherein, substituents are reported herein.

8 Claims, 10 Drawing Sheets
Specification includes a Sequence Listing.

```
Query   1   MTEYKLVVVGAGGVGKSALTIQLIQNHFVDEYDPTIEDSYRKQVVIDGETCLLDILDTAG  60
            MTEYKLVVVGAGGVGKSALTIQLIQNHFVDEYDPTIEDSYRKQVVIDGETCLLDILDTAG
Sbjct   1   MTEYKLVVVGAGGVGKSALTIQLIQNHFVDEYDPTIEDSYRKQVVIDGETCLLDILDTAG  60

Query  61   QEEYSAMRDQYMRTGEGFLCVFAINNTKSFEDIHHYREQIKRVKDSEDVPMVLVGNKCDL 120
            QEEYSAMRDQYMRTGEGFLCVFAINNTKSFEDIHHYREQIKRVKDSEDVPMVLVGNKCDL
Sbjct  61   QEEYSAMRDQYMRTGEGFLCVFAINNTKSFEDIHHYREQIKRVKDSEDVPMVLVGNKCDL 120

Query 121   PSRTVDTKQAQDLARSYGIPFIETSAKTRQGVDDAFYTLVREIRKHK-EKMSKDGKKKKK 179
            PSRTVDTKQAQDLARSYGIPFIETSAKTRQ V+DAFYTLVREIR+++ +K+SK+ K
Sbjct 121   PSRTVDTKQAQDLARSYGIPFIETSAKTRQRVEDAFYTLVREIRQYRLKKISKEEKTPGC 180

Query 180   KSKTKCVIM   188   SEQ ID NO: 1
                  KC+IM
Sbjct 181   VKIKKCIIM   189   SEQ ID NO: 2
```

FIG. 7

SEQUENCE LISTING

<160> NUMBER OF SEQ ID NOS: 3

<210> SEQ ID NO 1
<211> LENGTH: 188
<212> TYPE: PRT
<213> ORGANISM: Homo sapiens

<400> SEQUENCE: 1

```
Met Thr Glu Tyr Lys Leu Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
                115                 120                 125

Gln Ala Gln Asp Leu Ala Arg Ser Tyr Gly Ile Pro Phe Ile Glu Thr
                130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
                180                 185
```

<210> SEQ ID NO 2
<211> LENGTH: 189
<212> TYPE: PRT
<213> ORGANISM: Homo sapiens

<400> SEQUENCE: 2

```
Met Thr Glu Tyr Lys Leu Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
                115                 120                 125

Gln Ala Gln Asp Leu Ala Arg Ser Tyr Gly Ile Pro Phe Ile Glu Thr
```

```
            130                 135                 140
Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185
```

<210> SEQ ID NO 3
<211> LENGTH: 433
<212> TYPE: PRT
<213> ORGANISM: Homo sapiens

<400> SEQUENCE: 3

```
Met Glu Val Val Asp Pro Gln Gln Leu Gly Met Phe Thr Glu Gly Glu
1               5                   10                  15

Leu Met Ser Val Gly Met Asp Thr Phe Ile His Arg Ile Asp Ser Thr
            20                  25                  30

Glu Val Ile Tyr Gln Pro Arg Arg Lys Arg Ala Lys Leu Ile Gly Lys
        35                  40                  45

Tyr Leu Met Gly Asp Leu Leu Gly Glu Gly Ser Tyr Gly Lys Val Lys
    50                  55                  60

Glu Val Leu Asp Ser Glu Thr Leu Cys Arg Arg Ala Val Lys Ile Leu
65                  70                  75                  80

Lys Lys Lys Lys Leu Arg Arg Ile Pro Asn Gly Glu Ala Asn Val Lys
                85                  90                  95

Lys Glu Ile Gln Leu Leu Arg Arg Leu Arg His Lys Asn Val Ile Gln
            100                 105                 110

Leu Val Asp Val Leu Tyr Asn Glu Glu Lys Gln Lys Met Tyr Met Val
        115                 120                 125

Met Glu Tyr Cys Val Cys Gly Met Gln Glu Met Leu Asp Ser Val Pro
130                 135                 140

Glu Lys Arg Phe Pro Val Cys Gln Ala His Gly Tyr Phe Cys Gln Leu
145                 150                 155                 160

Ile Asp Gly Leu Glu Tyr Leu His Ser Gln Gly Ile Val His Lys Asp
                165                 170                 175

Ile Lys Pro Gly Asn Leu Leu Leu Thr Thr Gly Gly Thr Leu Lys Ile
            180                 185                 190

Ser Asp Leu Gly Val Ala Glu Ala Leu His Pro Phe Ala Ala Asp Asp
        195                 200                 205

Thr Cys Arg Thr Ser Gln Gly Ser Pro Ala Phe Gln Pro Pro Glu Ile
    210                 215                 220

Ala Asn Gly Leu Asp Thr Phe Ser Gly Phe Lys Val Asp Ile Trp Ser
225                 230                 235                 240

Ala Gly Val Thr Leu Tyr Asn Ile Thr Thr Gly Leu Tyr Pro Phe Glu
                245                 250                 255

Gly Asp Asn Ile Tyr Lys Leu Phe Glu Asn Ile Gly Lys Gly Ser Tyr
            260                 265                 270

Ala Ile Pro Gly Asp Cys Gly Pro Pro Leu Ser Asp Leu Leu Lys Gly
        275                 280                 285

Met Leu Glu Tyr Glu Pro Ala Lys Arg Phe Ser Ile Arg Gln Ile Arg
    290                 295                 300

Gln His Ser Trp Phe Arg Lys Lys His Pro Pro Ala Glu Ala Pro Val
305                 310                 315                 320
```

```
Pro Ile Pro Pro Ser Pro Asp Thr Lys Asp Arg Trp Arg Ser Met Thr
            325             330             335

Val Val Pro Tyr Leu Glu Asp Leu His Gly Ala Asp Glu Asp Glu Asp
            340             345             350

Leu Phe Asp Ile Glu Asp Asp Ile Ile Tyr Thr Gln Asp Phe Thr Val
            355             360             365

Pro Gly Gln Val Pro Glu Glu Glu Ala Ser His Asn Gly Gln Arg Arg
            370             375             380

Gly Leu Pro Lys Ala Val Cys Met Asn Gly Thr Glu Ala Ala Gln Leu
385             390             395             400

Ser Thr Lys Ser Arg Ala Glu Gly Arg Ala Pro Asn Pro Ala Arg Lys
            405             410             415

Ala Cys Ser Ala Ser Ser Lys Ile Arg Arg Leu Ser Ala Cys Lys Gln
            420             425             430

Gln
```

KRAS AGONISTS, PHARMACEUTICAL COMPOSITIONS, AND USES IN MANAGING CANCER

CROSS-REFERENCE TO RELATED APPLICATIONS

This application claims the benefit of U.S. Provisional Application No. 62/907,188 filed Sep. 27, 2019. The entirety of this application is hereby incorporated by reference for all purposes.

STATEMENT REGARDING FEDERALLY SPONSORED RESEARCH

This invention was made with government support under CA193828, CA136534, and CA200905 awarded by the National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy and is hereby incorporated by reference into the specification. The name of the text file containing the Sequence Listing is 19149US_ST25.txt. The text file is 8 KB, was created on Sep. 28, 2020 and is being submitted electronically via EFS-Web.

BACKGROUND

RAS family genes, including HRAS, KRAS and NRAS, are common oncogenes in human cancer, and encode similar proteins made up of chains of 188 to 189 amino acids. The sequences and structural features of these three proteins are conserved, except for their carboxyl-terminal domains and post-translational lipid modifications. The RAS genes encode monomeric GTPases that function as molecular switches in signal transduction pathways regulating cell proliferation, differentiation and survival in mammalian cells. Mutations that can constitutively activate RAS have been found in many different types of human cancers. KRAS has the highest mutation rate compared to HRAS and NRAS in various types of cancers.

KRAS binds to GTP in its active state and possesses an intrinsic enzymatic activity which cleaves the terminal phosphate of the nucleotide, converting it to GDP. Upon conversion of GTP to GDP, KRAS is deactivated. Currently, there are no effective targeted therapies for patients with KRAS mutant cancers. It is difficult to inhibit its intracellular activity because there is a picomolar affinity between KRAS and GTP while micromolar concentrations of GTP exist in cancer cells. Thus, there is a need to identify improved therapeutic methods and compositions.

Overmeyer et al. report death pathways triggered by activated Ras in cancer cells. Front Biosci (Landmark Ed). 2011, 16:1693-713. Ostrem et al. report K-Ras(G12C) inhibitors allosterically control GTP affinity and effector interactions. Nature. 2013, 503:548-51. Lito et al. report allele-specific inhibitors inactivate mutant KRAS G12C by a trapping mechanism. Science, 2016, 351(6273): 604-608. Patricelli et al. report selective inhibition of oncogenic KRAS output with small molecules targeting the inactive state. Cancer Discov, 2016, 6:316-29. Welsch et al. report multivalent small-molecule pan-RAS inhibitors. Cell, 2017, 168:878-889, e829. Peeters et al. report fructose-1,6-bisphosphate couples glycolytic flux to activation of Ras. Nat Commun, 2017, 8:922.

Baker et al. report irreversible inhibitors of dihydrofolic reductase and derivatives of p-alkyl and p-aralkyl benzoic acids. J Pharm Sci. 1967, 56(1):38-42. Lagoutte et al. report reversable and covalent inhibitors. Curr Opin Chem Biol, 2017, 39:54-63.

References cited herein are not an admission of prior art.

SUMMARY

In certain embodiments, this disclosure relates to KRAS agonists, pharmaceutical composition, and uses in managing cancer. In certain embodiments, the KRAS agonist is 4-(4-(2-bromoacetamido)butyl)benzoic acid, salt, prodrug, or derivative thereof. In certain embodiments, this disclosure relates to methods of treating cancer comprising administering an effective amount of a compound of Formula I,

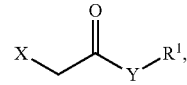

salt, prodrug, or derivative thereof, to a subject in need thereof, wherein, substituents are reported herein. In certain embodiments, the compound, salt, prodrug, or derivative thereof is administered in combination with an additional chemotherapy agent. In certain embodiments, the subject is diagnosed with multiple myeloma, leukemia, lymphoma, lung, pancreatic, colorectal, uterine, esophageal, gastric, cervical, or bladder cancer.

In certain embodiments, an effective amount is between 7.5 and 30 mg/kg/day or between 5 to 50 mg/kg/day, or 1 to 100 mg/kg/day. In certain embodiments, the subject is a human diagnosed with a KRAS mutation, or other RAS protein. In certain embodiments, the subject is diagnosed with a glycine to cysteine mutation at position 12, a glycine to aspartic acid at position 12, a glycine to arginine at position 12, a glycine to serine at position 12, a glycine to valine at position 12, or a glycine to aspartic acid at position 13, a glutamine to histidine at position 61, an alanine to threonine at position 146, or combinations thereof. In certain embodiments, the subject is diagnosed with a non-mutated lysine (K) in KRAS, or other RAS protein, at amino acid position 117. In certain embodiments, the KRAS mutation is diagnosed in combination with a LKB1 inactivating mutation.

In certain embodiments, this disclosure relates to methods of diagnosing and treating cancer comprising, identifying a KRAS mutation from a cancer cell from a subject diagnosed with cancer, diagnosing the subject as responsive to a therapy of a compound disclosed herein, and administering an effective amount of the compound to the subject.

In certain embodiments, this disclosure relates to methods of diagnosing and treating lung cancer comprising measuring quantities of RNAs from a lung cancer cell from a subject diagnosed with lung cancer, wherein the RNA is associated with all following genes KRAS and optionally/or LKB1, diagnosing the subject as responsive to a therapy of a compound disclosed herein when the measurements indicate increased quantities of mutated RNA compared to a normal cell; and administering an effective amount of the compound to the subject.

In certain embodiments, this disclosure relates to pharmaceutical compositions comprising a compound disclosed herein or salts thereof and a pharmaceutically acceptable excipient. In certain embodiments, the pharmaceutical composition is in the form of a tablet, capsule, pill, gel, granules, aerosol, or aqueous buffer, such as a saline or phosphate buffer, or a nanoparticle formulation, emulsion, liposome, etc. The pharmaceutical composition may also include one or more further active agents or may be administered in combination with one or more such active agent.

BRIEF DESCRIPTION OF THE DRAWINGS

FIG. 7 illustrates a sequence comparison of KRAS isoform b (SEQ ID NO: 1) and isoform a (SEQ ID NO: 2) which have sequence identity of 170/189 (90%) and similarity of 178/189 (94%).

DETAILED DESCRIPTION

Figure 1A:
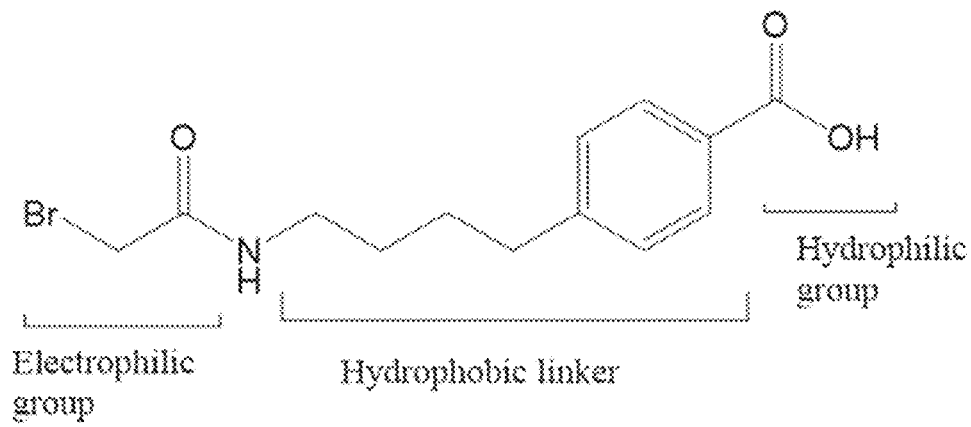
FIG. 1A illustrates the chemical structure of the KRAS agonist, KRA-533, and illustrates the chemical groups which may be characterized as an electrophilic group, a lipophilic group, and a hydrophilic group. Although it is not intended that embodiments of this disclosure be limited by any particular mechanism, it is possible that the electrophilic bromoacetamido group hydrogen bonds with the primary amino group of the amino acid lysine at position 117, (K117), or it is possible that the bromoacetamido group of KRA-533 reacts with the primary amino group of the amino acid lysine at K117 and irreversibly forms a covalent bond by bromide displacement.

Unless defined otherwise, all technical and scientific terms used herein have the same meaning as is commonly understood by one of ordinary skill in the art to which this disclosure belongs. In the event that there is a plurality of definitions for a term herein, those in this section prevail unless stated otherwise.

It is also to be understood that the terminology used herein is for the purpose of describing particular embodiments only, and is not intended to be limiting, since the scope of the present disclosure will be limited only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Embodiments of the present disclosure will employ, unless otherwise indicated, techniques of synthetic organic chemistry, biochemistry, biology, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

As used herein, "subject" refers any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

As used herein, the term "KRAS" refers to Kirsten ras oncogene homolog from the mammalian ras gene family that is a member of the small GTPase superfamily GTPase. Alternative splicing of KRAS gene expression leads to variants encoding two isoforms that differ in the C-terminal region. The predominant human isoform "b" NCBI Reference Sequence: NP_001356716.1, has the following amino acid sequence:

(SEQ ID NO: 1)
MTEYKLVVVGAGGVGKSALTIQLIQNHFVDEYDPTIEDSYRKQVVID

GETCLLDILDTAGQEEYSAMRDQYMRTGEGFLCVFAINNTKSFEDIH

HYREQIKRVKDSEDVPMVLVGNKCDLPSRTVDTKQAQDLARSYGIPF

IETSAKTRQGVDDAFYTLVREIRKHKEKMSKDGKKKKKKSKTKCVIM.

Human isoform "a" NCBI Reference Sequence: NP_001356715.1, has the following amino acid sequence, (SEQ ID NO: 2)
MTEYKLVVVGAGGVGKSALTIQLIQNHFVDEYDPTIEDSYRKQVVID

GETCLLDILDTAGQEEYSAMRDQYMRTGEGFLCVFAINNTKSFEDIH

HYREQIKRVKDSEDVPMVLVGNKCDLPSRTVDTKQAQDLARSYGIPF

IETSAKTRQRVEDAFYTLVREIRQYRLKKISKEEKTPGCVKIKKCII

M.

As used herein, the terms "diagnosed with an [amino acid] mutation at a position [number]," and like terms, refer to the detection the corresponding nucleotide mutation within the related gene DNA, mRNA, or detection of the mutant protein sequence by analysis of a sample of the subject. In the context of nucleotide detection, it is well-understood by skilled artisans that such an amino acid associated mutation refers to the necessary change of a nucleotide within the corollary DNA/RNA codon. As illustrated in FIG. 7, a "position" of an amino acid for KRAS is in relation to SEQ ID NO: 2. SEQ ID NO: 2 contains one additional amino acid when compared to SEQ ID NO: 1, i.e., SEQ ID NO:1 contains a deletion at amino acid position 168.

As used herein "LKB1," "STK11/LKB1," and like terms refer to a serine/threonine-protein kinase STK11 that encodes a serine threonine kinase that phosphorylates adenosine monophosphate-activated protein kinase (AMPK) and AMPK-related kinases. Inactivating mutations of STK11 (or its protein product, LKB1) are associated with resistance to chemotherapy agents in patients with non-small-cell lung cancer (NSCLC). Human NCBI Reference Sequence: NP_000446.1 has the following amino acid sequence:

(SEQ ID NO: 3)
MEVVDPQQLGMFTEGELMSVGMDTFIHRIDSTEVIYQPRRKRAKLIGK

YLMGDLLGEGSYGKVKEVLDSETLCRRAVKILKKKKLRRIPNGEANVK

KEIQLLRRLRHKNVIQLVDVLYNEEKQKMYMVMEYCVCGMQEMLDSVP

EKRFPVCQAHGYFCQLIDGLEYLHSQGIVHKDIKPGNLLLTTGGTLKI

SDLGVAEALHPFAADDTCRTSQGSPAFQPPEIANGLDTFSGFKVDIWS

AGVTLYNITTGLYPFEGDNIYKLFENIGKGSYAIPGDCGPPLSDLLKG

MLEYEPAKRFSIRQ1RQHSWFRKKHPPAEAPVPIPPSPDTKDRWRSMT

VVPYLEDLHGADEDEDLFDIEDDIIYTQDFTVPGQVPEEEASHNGQRR

GLPKAVCMNGTEAAQLSTKSRAEGRAPNPARKACSASSKIRRLSACKQQ.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In certain embodiments, the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulphur atom or replacing an amino group with a hydroxyl group. The derivative may be a prodrug. Derivatives may be prepared by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —$NR_aR_b$, —$NR_aC(=O)R_b$, —$NR_aC(=O)NR_aNR_b$, —$NR_aC(=O)OR_b$, —$NR_aSO_2R_b$, —$C(=O)R_a$, —$C(=O)OR_a$, —$C(=O)NR_aR_b$, —$OC(=O)NR_aR_b$, —$OR_a$, —$SR_a$, —$SOR_a$, —$S(=O)_2R_a$, —$OS(=O)_2R_a$ and —$S(=O)_2OR_a$. $R_a$ and $R_b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, or heteroarylalkyl.

As used herein, the term "prodrug" refers a compound that, after administration, is metabolized (i.e., converted within the body) into a pharmacologically active drug. Examples include alkoxy esters of hydroxyl groups or carboxyl groups such as acetate esters, benzoate esters, alkyl ethers, amino acids esters, glycolic acid esters, malic acid esters, acyloxyalkyl esters, alkoxycarbonyloxy alkyl esters, S-acylthioalkyl esters, hydroxylamine amides, phosphonylmethoxy ethers, phosphates, phosphoramidates, and combinations thereof.

As used herein, a "lipid" group refers to a hydrophobic group that is naturally or non-naturally occurring that is highly insoluble in water. As used herein a lipid group is considered highly insoluble in water when the point of connection on the lipid is replaced with a hydrogen and the resulting compound has a solubility of less than 0.63×10−4% w/w (at 25° C.) in water, which is the percent solubility of octane in water by weight. See Solvent Recovery Handbook, 2nd Ed, Smallwood, 2002 by Blackwell Science, page 195. Examples of naturally occurring lipids include saturated or unsaturated hydrocarbon chains found in fatty acids, glycerolipids, cholesterol, steroids, polyketides, and derivatives. Non-naturally occurring lipids include derivatives of naturally occurring lipids, acrylic polymers, aromatic, and alkylated compounds and derivatives thereof.

A "linking group" refers to any variety of molecular arrangements that can be used to bridge two molecular moieties together. An example formula may be —$R_m$— wherein R is selected individually and independently at each occurrence as: —$CR_mR_m$—, —$CHR_m$—, —CH—, —C—, —$CH_2$—, —$C(OH)R_m$—, —C(OH)(OH)—, —C(OH)H, —$C(Hal)R_m$—, —C(Hal)(Hal)-, —C(Hal)H—, —C(CN)$R_m$—, —C(CN)(CN)—, —C(CN)H—, —O—, —S—, —N—, —NH—, —$NR_m$—, —(C=O)—, —(C=NH)—, —(C=S)—, —(C=$CH_2$)—, which may contain single, double, or triple bonds individually and independently between the R groups. If an R is branched with an $R_m$ it may be terminated with a group such as —$CH_3$, —H, —CH=$CH_2$, —CCH, —OH, —SH, —$NH_2$, —CN, or —Hal, or two branched Rs may form a cyclic structure. It is contemplated that in certain instances, the total Rs or "m" may be less than 100 or 50 or 25 or 10. Examples of linking groups in include bridging alkyl groups and alkoxyalkyl groups.

As used herein, "alkyl" means a noncyclic straight chain or branched, unsaturated or saturated hydrocarbon such as those containing from 1 to 25 carbon atoms. For example, a "C8-C18" refers to an alkyl containing 8 to 18 carbon atoms. Likewise, a "C6-C22" refers to an alkyl containing 6 to 22 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulphur which may be saturated or unsaturated (but not aromatic), monocyclic or polycyclic, and wherein the nitrogen and sulphur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, and the like.

The term "aryl" refers to aromatic homocyclic (i.e., hydrocarbon) mono-, bi- or tricyclic ring-containing groups preferably having 6 to 12 members such as phenyl, naphthyl and biphenyl. Phenyl is a preferred aryl group.

As used herein, "heteroaryl" or "heteroaromatic" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkoxy" refers to an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkoxyalkyl" refers an alkyl group as defined above with the indicated number of carbon atoms attached through an alkyl bridge (i.e., —CH$_2$—O—CH$_2$CH$_3$).

"Alkylamino" refers an alkyl group as defined above with the indicated number of carbon atoms attached through an amino bridge. An example of an alkylamino is methylamino, (i.e., —NH—CH3).

"Alkylthio" refers to an alkyl group as defined above with the indicated number of carbon atoms attached through a sulfur bridge. An example of an alkylthio is methylthio, (i.e., —S—CH$_3$).

"Alkanoyl" refers to an alkyl as defined above with the indicated number of carbon atoms attached through a carbonyl bride (i.e., —(C=O)alkyl).

The terms "cycloalkyl" and "cycloalkenyl" refer to mono-, bi-, or tri homocyclic ring groups of 3 to 15 carbon atoms which are, respectively, fully saturated and partially unsaturated.

"Alkylsulfonyl" refers to an alkyl as defined above with the indicated number of carbon atoms attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfamoyl" refers to an alkyl as defined above with the indicated number of carbon atoms attached through a sulfamoyl bridge (i.e., —NHS(=O)$_2$alkyl), and an "Arylsulfamoyl" refers to an alkyl attached through a sulfamoyl bridge (i.e., (i.e., —NHS(=O)$_2$aryl).

"Alkylsulfinyl" refers to an alkyl as defined above with the indicated number of carbon atoms attached through a sulfinyl bridge (i.e. —S(=O)alkyl).

The terms "halogen" and "halo" refer to fluorine, chlorine, bromine, and iodine.

As used herein the terms, "electrophile" or "electrophilic group" refer to a molecule or group of molecules that accepts a pair of electrons from a nucleophile to make a reversable or irreversible covalent bond under physiological conditions. Electrophiles include molecules with formal positive charge or a partial positive charge, under physiological conditions. In the context of a group of molecules, a partial positive charge is typically due to the proximity to a polar bond (e.g., a carbonyl or double bond or triple bond). Examples of electrophilic groups in physiological conditions include alpha-haloacetyl, alkenylsulfonyl, acryl, propiolyl, oxiranyl, and nitropropenyl groups. Examples of nucleophilic groups in physiological conditions include primary amines and thiols. Peptide side groups that act as nucleophiles include amino acids such as cysteine, histidine, and lysine.

As used herein the term, "leaving group" refers to a molecule or group of molecules that is displaced by the breaking of a covalent bond within a compound when an electrophile within the compound accepts a pair of electrons from a nucleophile to form a new bond. Examples of leaving groups include halogen ions, carboxylate ions, sulfonate ions, and water.

KRAS Agonists

In certain embodiments, this disclosure relates to KRAS agonists disclosed herein and pharmaceutical compositions comprising the same. In certain embodiments, the KRAS agonist is 4-(4-(2-bromoacetamido)butyl)benzoic acid, salt, prodrug, or derivative thereof. In certain embodiments the KRAS agonist is a compound with an electrophilic group and a hydrophilic group connected together by a lipophilic linker.

In certain embodiments, the KRAS agonist is a compound of Formula I,

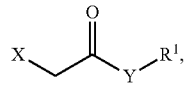

Formula I salt, prodrug, or derivative thereof, to a subject in need thereof, wherein, X is halogen or other leaving group;

Y is NH, absent, or a linking group;

R$^1$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein R$^1$ is optionally substituted with one or more, the same or different, R$^{10}$;

R$^{10}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein R$^{10}$ is optionally substituted with one or more, the same or different, R$^{11}$;

R$^{11}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein R$^{11}$ is optionally substituted with one or more, the same or different, R$^{12}$;

R$^{12}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein R$^{12}$ is optionally substituted with one or more, the same or different, R$^{13}$; and R$^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, X is a halogen,

In certain embodiments, Y is NH.

In certain embodiments, Y is NH or other linking group;

In certain, embodiments, $R^1$ is lipid substituted with a hydrophilic group, such as an alkyl substituted with an aryl wherein the aryl is substituted with a hydrophilic group, such as one or more carboxylic acid or hydroxyl groups, optionally in a prodrug form.

In certain embodiments, this disclosure contemplates that $R^1$ is a lipid substituted with a hydrophilic group such as one or more carboxylic acid or hydroxyl groups, optionally in a prodrug form.

In certain embodiments, the KRAS agonist is a compound of Formula IA,

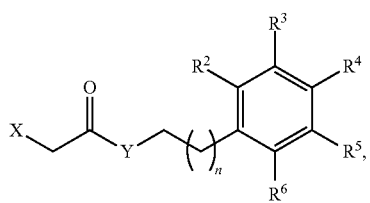

Formula IA salt, prodrug, or derivative thereof to a subject in need thereof, wherein, X is halogen or other leaving group;

Y is a absent, NH, or a linking group;

n is 1 to 5;

$R^2$, $R^3$, $R^4$, $R^5$, and $R^6$ are each individually and independently selected from hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^2$, $R^3$, $R^4$, $R^5$, and $R^6$ are optionally substituted with one or more, the same or different, $R^{11}$;

$R^{11}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$; and $R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, 2-methoxyethoxy, 2-hydroxyethoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^3$, $R^4$, and/or $R^5$, are a hydrophilic group such as a carboxylic acid or hydroxyl group optionally in prodrug form.

In certain embodiments, $R^4$ is a hydrophilic group such as a carboxylic acid or hydroxyl group optionally in prodrug form.

Mutant KRAS Cancer Therapy

KRAS binds to GTP in its active state and possesses an intrinsic enzymatic activity which cleaves the terminal phosphate of the nucleotide, converting it to GDP. Upon conversion of GTP to GDP, KRAS is deactivated. The rate of conversion is usually slow but can be increased dramatically by an accessory GTPase-activating protein (GAP). In turn, KRAS can bind to guanine nucleotide exchange factors (GEFs) (such as SOS), which force the release of bound nucleotide (GDP). GTP binding enables several residues, primarily in the switch I region (residues 30-40) and switch II region (residues 60-70), to adopt a conformation that permits KRAS effector proteins to bind; these switches are regulated by GAPs and GEFs. In mammalian cells, endogenous KRAS proteins are predominantly in the GDP state and activation is transient. However, the common oncogenic mutations in KRAS proteins interfere with GTP hydrolysis, resulting in proteins that remain in the active GTP state and continue to transmit signals to effector pathways. Thus, KRAS acts as a molecular on/off switch. Once it is turned on, it recruits and activates proteins necessary for the propagation of signaling of growth factors and other receptors, such as c-Raf and PI3K.

Somatic KRAS mutations are found at high rates in leukemia, colorectal cancer, pancreatic cancer and non-small cell lung cancer (NSCLC). In NSCLC, KRAS mutation is observed in up to 30-40% of cases. The most common KRAS mutations include G12C, G12D, G12R, G12S, G12 V, G13D and Q61H. Beyond the most common hotspot alleles in exons 2 and 3, mutations in exon 4 of KRAS, including K117N and A146T, have also been found in patients with colorectal cancer. KRAS mutations constitutively activate KRAS and subsequently its downstream Raf/MEK/ERK1/2 and PI3K/PIP3/AKT survival pathways in various cancers, including lung cancer. Experimental evidence supports a paradoxical role for RAS proteins in the initiation of cell death pathways. Hyperactive RAS forces cells into the pathway of programmed cell death. Vitamin C treatment selectively kills mutant KRAS expressing tumor cells, but not wild-type KRAS containing cells. Interestingly, either glucose withdrawal or glucose-mediated hyperactivation of RAS is able to trigger apoptosis. RAS oncogenes trigger apoptosis only under specific conditions. Thus, manipulation of the opposing functions of KRAS in cell proliferation/survival versus cell death should be an attractive approach for the treatment of various types of cancers, especially those with mutant KRAS. Creation of therapeutic agents that directly inhibit the oncogenic effects of RAS proteins has been challenging.

KRA-533 potently enhances intracellular KRAS activities to various degrees in a series of human NSCLC cell lines in association with various degrees of growth inhibition. Intriguingly, lung cancer cell lines bearing KRAS mutation are more sensitive to KRA-533 than those without KRAS mutation, indicating KRA-533 may be relatively selective for mutant KRAS lung cancer cells. KRA-533 not only directly binds to WT KRAS protein but also KRAS mutants, including G12C, G12D and G13D. Although KRAS mutants have higher levels of activities than WT KRAS before KRA-533 treatment, KRA-533 induces a dose-dependent increase in activity of WT and mutant KRAS in cell-free GDP-GTP exchange assay and in lung cancer cells. Compared to WT KRAS, the G12C, G12D and G13D KRAS mutants become hyperactive following KRA-533 treatment. It has been reported that glucose withdrawal or glucose-mediated hyperactivation of RAS is able to trigger apoptosis. Hyperactivation of RAS can also trigger autophagy-associated cell death. KRA-533-induced hyperactivation of mutant KRAS led to apoptosis and autophagic cell death in mutant KRAS lung cancer cell lines (i.e. A549, H157 and Calu-1). In contrast, the moderate level of WT KRAS activation induced by KRA-533 caused significantly less apoptosis and autophagic cell death in a lung cancer cell line without KRAS mutation (i.e. H292). Therefore, there may be a threshold of KRAS activity in cells to dictate pathway choice between survival and death. Although it is not intended that embodiments of this disclosure be limited by any particular mechanism, KRAS activity at or below a certain threshold may promote cell survival and proliferation while KRAS activity beyond the threshold (i.e. hyperactivation or super-activity) may promote cell death. KRA-533 may change the nature of KRAS signaling from pro-survival to pro-death by stimulating active mutant KRAS to a super-active status that is beyond the activity threshold.

Data indicates that KRA-533 not only binds KRAS but also directly activates its activity. Structural modeling analysis by computational programming reveals that KRA-533 is associated with 15 amino acids in the GDP/GTP binding pocket, including the hydrogen-bond predicted with residue K117. Mutation of K117 to Ala resulted in KRAS loss of KRA-533 binding capacity. KRA-533 failed to activate K117A mutant KRAS.

KRA-533 exhibited potent antitumor activity against mutant KRAS lung cancer via induction of KRAS hyperactivation, apoptosis and autophagic cell death in NSCLC xenografts. The dose range between 10 and 30 mg/kg/day was effective without significant normal tissue toxicity in murine lung cancer models. The potency of KRA-533 was evaluated in genetically engineered LSL-KRASG12D and LSL-KRASG12D LKB1fl/fl (KL) mice. KRA-533 significantly reduces tumor burden in the lungs of both LSL-KRASG12D and KL mice, leading to prolonged survival compared to the untreated control group, suggesting that KRA-533 has potential to improve the prognosis of mutant KRAS driven lung cancer.

In certain embodiments, this disclosure contemplates a KRAS agonist compound or composition as disclosed herein for use in treating cancer. In certain embodiments, this disclosure contemplates methods of treating cancer comprising administering an effective amount of a compound or a composition as disclosed herein to a subject in need thereof. In certain embodiments, the subject is at risk of, exhibiting symptoms of, or diagnosed with cancer. In certain embodiments, the compound is administered in combination with another anti-cancer agent.

In certain embodiments, this disclosure contemplates compound or composition as disclosed herein in the production of a medicament for use in treating cancer. "Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" may be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample compound compared to a control without the compound. It may also be identified by a change in relevant biomarker or gene expression profile, such as PSA for prostate cancer, HER2 for breast cancer, or others.

The cancer to be treated in the context of the present disclosure may be any type of cancer or tumor. These tumors or cancer include, and are not limited to, tumors of the hematopoietic and lymphoid tissues or hematopoietic and lymphoid malignancies, tumors that affect the blood, bone marrow, lymph, and lymphatic system. Hematological malignancies may derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are from the lymphoid line, while acute and chronic myelogenous leukemia, myelodysplastic syndromes and myeloproliferative diseases are myeloid in origin.

Also contemplated are malignancies located in the colon, abdomen, bone, breast, digestive system, liver, pancreas, peritoneum, endocrine glands (adrenal, parathyroid, hypophysis, testicles, ovaries, thymus, thyroid), eye, head and neck, nervous system (central and peripheral), lymphatic system, pelvis, skin, soft tissue, spleen, thorax and genito-urinary apparatus and, more particularly, childhood acute lymphoblastic leukemia, acute lymphoblastic leukemia, acute lymphocytic leukemia, acute myeloid leukemia, adrenocortical carcinoma, adult (primary) hepatocellular cancer, adult (primary) liver cancer, adult acute lymphocytic leukemia, adult acute myeloid leukemia, adult Hodgkin's disease, adult Hodgkin's lymphoma, adult lymphocytic leukemia, adult non-Hodgkin's lymphoma, adult primary liver cancer, adult soft tissue sarcoma, AIDS-related lymphoma, AIDS-related malignant tumors, anal cancer, astrocytoma, cancer of the biliary tract, cancer of the bladder, bone cancer, brain stem glioma, brain tumors, breast cancer, cancer of the renal pelvis and ureter, primary central nervous system lymphoma, central nervous system lymphoma, cerebellar astrocytoma, brain astrocytoma, cancer of the cervix, childhood (primary) hepatocellular cancer, childhood (primary) liver cancer, childhood acute lymphoblastic leukemia, childhood acute myeloid leukemia, childhood brain stem glioma, childhood cerebellar astrocytoma, childhood brain astrocytoma, childhood extracranial germ cell tumors, childhood Hodgkin's disease, childhood Hodgkin's lymphoma, childhood visual pathway and hypothalamic glioma, childhood lymphoblastic leukemia, childhood medulloblastoma, childhood non-Hodgkin's lymphoma, childhood supratentorial primitive neuroectodermal and pineal tumors, childhood primary liver cancer, childhood rhabdomyosarcoma, childhood soft tissue sarcoma, childhood visual pathway and hypothalamic glioma, chronic lymphocytic leukemia, chronic myeloid leukemia, cancer of the colon, cutaneous T-cell lymphoma, endocrine pancreatic islet cells carcinoma, endometrial cancer, ependymoma, epithelial cancer, cancer of the esophagus, Ewing's sarcoma and related tumors, cancer of the exocrine pancreas, extracranial germ cell tumor, extragonadal germ cell tumor, extrahepatic biliary tract cancer, cancer of the eye, breast cancer in women, Gaucher's disease, cancer of the gallbladder, gastric cancer, gastrointestinal carcinoid tumor, gastrointestinal tumors, germ cell tumors, gestational trophoblastic tumor, head and neck cancer, hepatocellular cancer, Hodgkin's disease, Hodgkin's lymphoma, hypergammaglobulinemia, hypopharyngeal cancer, intestinal cancers, intraocular melanoma, islet cell carcinoma, islet cell pancreatic cancer, Kaposi's sarcoma, cancer of kidney, cancer of the larynx, cancer of the lip and mouth, cancer of the liver, cancer of the lung, lymphoproliferative disorders, macroglobulinemia, breast cancer in men, malignant mesothelioma, malignant thymoma, medulloblastoma, melanoma, mesothelioma, occult primary metastatic squamous neck cancer, primary metastatic squamous neck cancer, metastatic squamous neck cancer, multiple myeloma, multiple myeloma/plasmatic cell neoplasia, myelodysplastic syndrome, myelogenous leukemia, myeloid leukemia, myeloproliferative disorders, paranasal sinus and nasal cavity cancer, nasopharyngeal cancer, neuroblastoma, non-Hodgkin's lymphoma during pregnancy, non-melanoma skin cancer, non-small cell lung cancer, metastatic squamous neck cancer with occult primary, buccopharyngeal cancer, malignant fibrous histiocytoma, malignant fibrous osteosarcoma/histiocytoma of the bone, epithelial ovarian cancer, ovarian germ cell tumor, ovarian low malignant potential tumor, pancreatic cancer, paraproteinemias, purpura, parathyroid cancer, cancer of the penis, hypophysis tumor, neoplasia of plasmatic cells/multiple myeloma, primary central nervous system lymphoma, primary liver cancer, prostate cancer, rectal cancer, renal cell cancer, cancer of the renal pelvis and ureter, retinoblastoma, rhabdomyosarcoma, cancer of the salivary glands, sarcoidosis, sarcomas, skin cancer, small cell lung cancer, small intestine cancer, soft tissue sarcoma, squamous neck cancer, stomach cancer, pineal and supratentorial primitive neuroectodermal tumors, T-cell lymphoma, testicular cancer, thymoma, thyroid cancer, transitional cell cancer of the renal pelvis and ureter, transitional renal pelvis and ureter cancer, trophoblastic tumors, cell cancer of the renal pelvis and ureter, cancer of the urethra, cancer of the uterus, uterine sarcoma, vaginal cancer, optic pathway and hypothalamic glioma, cancer of the vulva, Waldenstrom's macroglobulinemia, Wilms' tumor and any other hyperproliferative disease, as well as neoplasia, located in the system of a previously mentioned organ.

In certain embodiments, compounds disclosed herein may be administered in combination with an additional anti-cancer agent. A "chemotherapy agent," "chemotherapeutic," "anti-cancer agent" or the like, refer to molecules that are recognized to aid in the treatment of a cancer. Contemplated examples include the following molecules or derivatives such as abemaciclib, abiraterone acetate, methotrexate, paclitaxel, adriamycin, acalabrutinib, brentuximab vedotin, ado-trastuzumab emtansine, aflibercept, afatinib, netupitant, palonosetron, imiquimod, aldesleukin, alectinib, alemtuzumab, pemetrexed disodium, copanlisib, melphalan, brigatinib, chlorambucil, amifostine, aminolevulinic acid, anastrozole, apalutamide, aprepitant, pamidronate disodium, exemestane, nelarabine, arsenic trioxide, ofatumumab, atezolizumab, bevacizumab, avelumab, axicabtagene ciloleucel, axitinib, azacitidine, carmustine, belinostat, bendamustine, inotuzumab ozogamicin, bevacizumab, bexarotene, bicalutamide, bleomycin, blinatumomab, bortezomib, bosutinib, brentuximab vedotin, brigatinib, busulfan, irinotecan, capecitabine, fluorouracil, carboplatin, carfilzomib, ceritinib, daunorubicin, cetuximab, cisplatin, cladribine, cyclophosphamide, clofarabine, cobimetinib, cabozantinib-S-malate, dactinomycin, crizotinib, ifosfamide, ramucirumab, cytarabine, dabrafenib, dacarbazine, decitabine, daratumumab, dasatinib, defibrotide, degarelix, denileukin diftitox, denosumab, dexamethasone, dexrazoxane, dinutuximab, docetaxel, doxorubicin, durvalumab, rasburicase, epirubicin, elotuzumab, oxaliplatin, eltrombopag olamine, enasidenib, enzalutamide, eribulin, vismodegib, erlotinib, etoposide, everolimus, raloxifene, toremifene, panobinostat, fulvestrant, letrozole, filgrastim, fludarabine, flutamide, pralatrexate, obinutuzumab, gefitinib, gemcitabine, gemtuzumab ozogamicin, glucarpidase, goserelin, propranolol, trastuzumab, topotecan, palbociclib, ibritumomab tiuxetan, ibrutinib, ponatinib, idarubicin, idelalisib, imatinib, talimogene laherparepvec, ipilimumab, romidepsin, ixabepilone, ixazomib, ruxolitinib, cabazitaxel, palifermin, pembrolizumab, ribociclib, tisagenlecleucel, lanreotide, lapatinib, olaratumab, lenalidomide, lenvatinib, leucovorin, leuprolide, lomustine, trifluridine, olaparib, vincristine, procarbazine, mechlorethamine, megestrol, trametinib, temozolomide, methylnaltrexone bromide, midostaurin, mitomycin C, mitoxantrone, plerixafor, vinorelbine, necitumumab, neratinib, sorafenib, nilutamide, nilotinib, niraparib, nivolumab, tamoxifen, romiplostim, sonidegib, omacetaxine, pegaspargase, ondansetron, osimertinib, panitumumab, pazopanib, interferon alfa-2b, pertuzumab, pomalidomide, mercaptopurine, regorafenib, rituximab, rolapitant, rucaparib, siltuximab, sunitinib, thioguanine, temsirolimus, thalidomide, thiotepa, trabectedin, valrubicin, vandetanib, vinblastine, vemurafenib, vorinostat, zoledronic acid, or combinations thereof such as cyclophosphamide, methotrexate, 5-fluorouracil (CMF); doxorubicin, cyclophosphamide (AC); mustine, vincristine, procarbazine, prednisolone (MOPP); sdriamycin, bleomycin, vinblastine, dacarbazine (ABVD); cyclophosphamide, doxorubicin, vincristine, prednisolone (CHOP); rituximab, cyclophosphamide, doxorubicin, vincristine, prednisolone (RCHOP); bleomycin, etoposide, cisplatin (BEP); epirubicin, cisplatin, 5-fluorouracil (ECF); epirubicin, cisplatin, capecitabine (ECX); methotrexate, vincristine, doxorubicin, cisplatin (MVAC).

In certain embodiments, the chemotherapy agent is an anti-PD-1, anti-CTLA4 antibody or combinations thereof, such as an anti-CTLA4 (e.g., ipilimumab, tremelimumab) or an anti-PD1 antibody (e.g., nivolumab, pembrolizumab, atezolizumab, avelumab, durvalumab).

Pharmaceutical Compositions

Pharmaceutical compositions typically comprise an effective amount of compounds and a suitable pharmaceutical acceptable carrier. The preparations can be prepared in a manner known per se, which usually involves mixing the compounds according to the disclosure with the one or more pharmaceutically acceptable carriers, and, if desired, in combination with other pharmaceutical active compounds, when necessary under aseptic conditions. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

The composition comprising compound disclosed herein can be administered to a subject either alone or as a part of a pharmaceutical composition. In certain embodiments, the pharmaceutical composition is in the form of a tablet, pill, capsule, gel, gel capsule or cream. In certain embodiments, the pharmaceutical composition is in the form of a sterilized pH buffered aqueous salt solution or a saline phosphate buffer between a pH of 6 to 8, optionally comprising a saccharide or polysaccharide.

In certain embodiments, the pharmaceutically acceptable excipient is selected from lactose, sucrose, mannitol, triethyl citrate, dextrose, cellulose, methyl cellulose, ethyl cellulose, hydroxyl propyl cellulose, hydroxypropyl methylcellulose, carboxymethylcellulose, croscarmellose sodium, polyvinyl N-pyrrolidone, crospovidone, ethyl cellulose, povidone, methyl and ethyl acrylate copolymer, polyethylene glycol, fatty acid esters of sorbitol, lauryl sulfate, gelatin, glycerin, glyceryl monooleate, silicon dioxide, titanium dioxide, talc, corn starch, carnauba wax, stearic acid, sorbic acid, magnesium stearate, calcium stearate, castor oil, mineral oil, calcium phosphate, starch, carboxymethyl ether of starch, iron oxide, triacetin, acacia gum, esters, or salts thereof.

In certain embodiments, pharmaceutical composition is in solid form surrounded by an enteric coating. In certain embodiments, the enteric coatings comprise methyl acrylate-methacrylic acid copolymers, cellulose acetate phthalate (CAP), cellulose acetate succinate, hydroxypropyl methyl cellulose phthalate, hydroxypropyl methyl cellulose acetate succinate (hypromellose acetate succinate), polyvinyl acetate phthalate (PVAP), methyl methacrylate-methacrylic acid copolymers, or combinations thereof.

The pharmaceutical compositions of the present disclosure can be administered to subjects either topically to the skin, orally, rectally, parenterally (intravenously, intramuscularly, or subcutaneously), intracisternally, intravaginally, intraperitoneally, intravesically, locally (powders, ointments, or drops), or as a buccal or nasal spray. Pharmaceutically acceptable salts, solvates and hydrates of the compounds listed are also useful in the method of the disclosure and in pharmaceutical compositions of the disclosure.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents solvents or vehicles include water, ethanol, polyols (propylene glycol, polyethylene glycol, glycerol, and the like), suitable mixtures thereof, vegetable (such as olive oil, sesame oil) and injectable organic esters such as ethyl oleate.

These compositions may also contain adjuvants such as preserving, emulsifying, and dispensing agents. Prevention of the action of microorganisms may be controlled by addition of any of various antibacterial and antifungal agents, example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders and granules. In such solid dosage forms, the active compound is admixed with at least one inert customary excipient (or carrier) such as sodium citrate or dicalcium phosphate or: (a) fillers or extenders, as for example, starches, lactose, sucrose, glucose, mannitol and silicic acid, (b) binders, as for example, carboxymethylcellulose, alginates, gelatin, polyvinylpyrrolidone, sucrose, and acacia, (c) humectants, as for example, glycerol (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar and as high molecular weight polyethylene glycols, and the like.

Solid dosage forms such as tablets, capsules, pills, and granules can be prepared with coatings and shells, such as enteric coatings and others well known in the art. They may contain opacifying agents and can also be of such composition that they release the active compound or compounds in a certain part of the intestinal tract in a delayed manner. Controlled slow release formulations are also preferred, including osmotic pumps and layered delivery systems.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethylene glycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions may contain suspending agents, as for example, ethoxylated iso-stearyl alcohols, polyoxyethylene sorbitol and sorbitan esters, microcrystalline cellulose, aluminum hydroxide, bentonite agar-agar and tragacanth, or mixtures of these substances, and the like.

Compositions for rectal administrations are preferably suppositories that can be prepared by mixing the compounds of the present disclosure with suitable nonirritating excipients or carriers such as cocoa butter, polyethylene glycol or a suppository wax, which are solid at ordinary temperatures but liquid at body temperature and therefore, melt in the rectum or vaginal cavity and release the active component.

Dosage forms for compound disclosed herein include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this disclosure.

Pharmaceutical compositions typically a compound disclosed herein and a suitable pharmaceutical acceptable carrier. The preparations can be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences. It is well known that ester prodrugs are readily degraded in the body to release the corresponding alcohol. See e.g., Imai, Drug Metab Pharmacokinet. (2006) 21(3):173-85, entitled "Human carboxylesterase isozymes: catalytic properties and rational drug design.

The pharmaceutical preparations of the disclosure are preferably in a unit dosage form, and can be suitably packaged, for example in a box, blister, vial, bottle, sachet, ampoule or in any other suitable single-dose or multi-dose holder or container (which can be properly labeled); optionally with one or more leaflets containing product information and/or instructions for use. Generally, such unit dosages will contain between 1 and 1000 mg, and usually between 5 and 500 mg, of the at least one compound of the disclosure e.g., about 10, 25, 50, 100, 200, 300 or 400 mg per unit dosage.

EXAMPLES

Screening of Small Molecules that Target the GTP/GDP Binding Pocket of KRAS

Figure 1B:
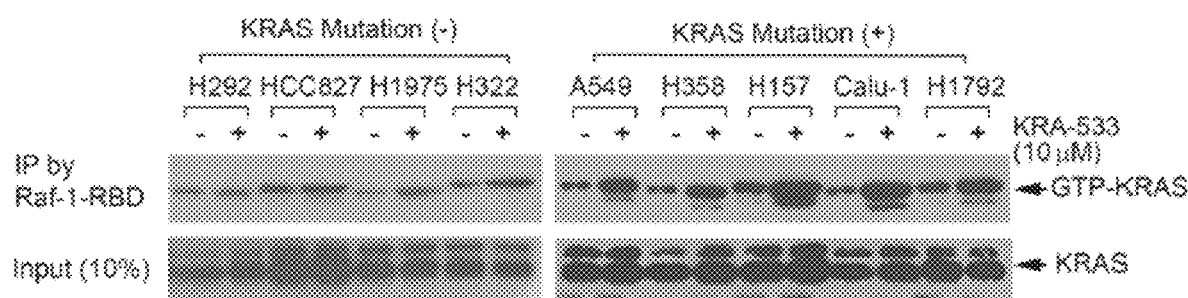
FIG. 1B shows data when various NSCLC cells with or without KRAS mutation were treated with KRA-533 (10 µM) for 48 h. KRAS-GTP (active form of KRAS) was pulled down by Raf-1-RBD, followed by Western blot using KRAS antibody.
Figure 1C:
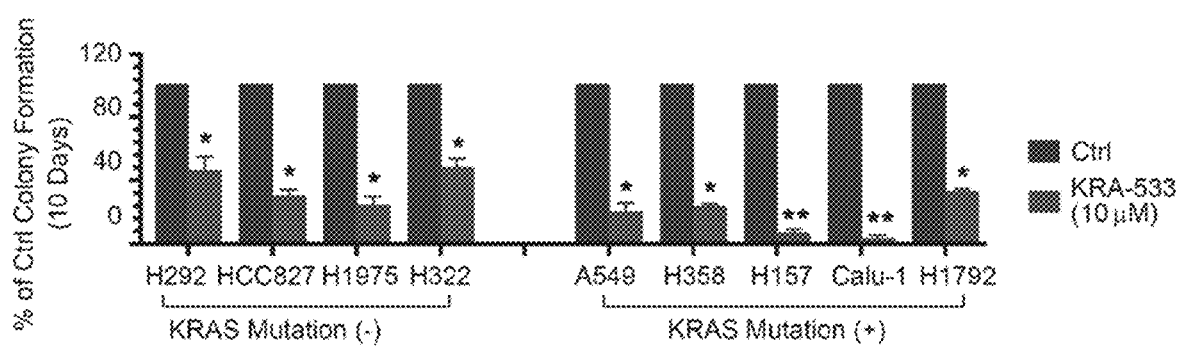
FIG. 1C shows data when various NSCLC cells were treated with KRA-533 (10 µM) for 10 days, followed by colony formation assay with quantification. This data indicates KRA-533 activates KRAS in association with growth inhibition of NSCLC cells.

A library containing small molecules from the National Cancer Institute (NCI) was employed to dock the GTP/GDP binding pocket of KRAS (PDB ID code: 4EPT) using the University of California, San Francisco (UCSF) DOCK 6.1 program suite. The small molecules were ranked according to their energy scores. Top 500 small molecules with predicted binding energies were selected for screening of cytotoxicity in human lung cancer cells by sulforhodamine B (SRB) assay. Among these small molecules, the compound NSC112533 (C13H16BrNO3, molecular weight [MW] 314.17) had the most potent activity against human lung cancer cells. This lead compound was named KRAS agonist-533 (KRA-533) (FIG. 1A). To test whether KRA-533 regulates KRAS activity in lung cancer cells, human lung cancer cell lines with or without KRAS mutation were treated with KRA-533 (10 μM) for 48 h. GTP-KRAS (active form of KRAS) was pulled down using Raf-1-RBD beads, followed by Western blot using KRAS antibody. KRA-533 enhanced KRAS activity in most human lung cancer cell lines tested, except H292. Intriguingly, KRA-533 enhanced KRAS activity to a greater extent in cell lines bearing KRAS mutation than in cell lines without KRAS mutation (FIG. 1). Colony formation analysis following 10-day's treatment revealed that human lung cancer cell lines with KRAS mutation (i.e. A549, H358, H157, Calu-1 and H1972) were relatively more sensitive to KRA-533-mediated cell growth suppression than those without KRAS mutation (i.e. H292, HCC827, H1975 and H322) (FIG. 1C). Cell proliferation was also measured following treatment of cells for 48 h using MTS Cell Proliferation Colorimetric Assay Kit. Treatment of various NSCLC cells with KRA-533 resulted in suppression of cell proliferation. Similarly, A549, H157 and Calu-1 cell lines bearing KRAS mutation were more sensitive to KRA-533 than H292 cells without KRAS mutation. These findings suggest that KRA-533 may be more suitable to treat mutant KRAS lung cancer.

Figure 2A:
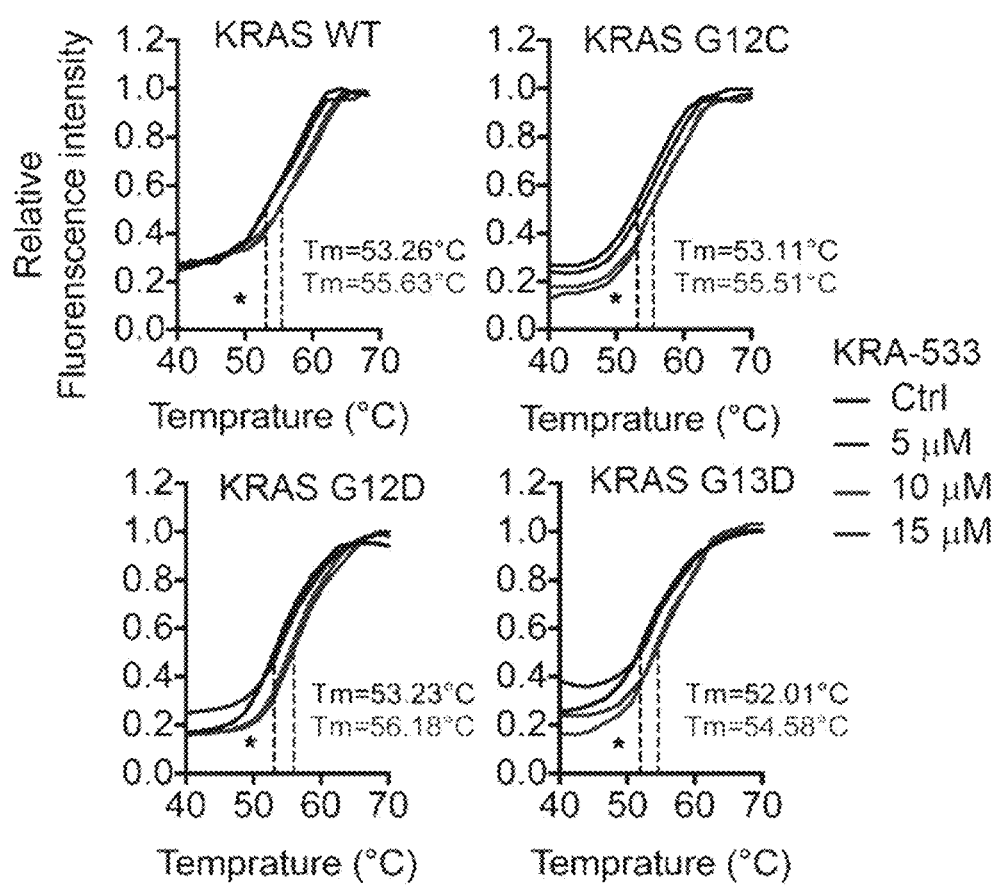
FIG. 2A shows thermal shift melting curves of purified KRAS proteins (WT, G12C, G12D or G13D) incubated with increasing concentrations of KRA-533. Melting temperature (Tm) values of DMSO Ctrl and 15 µM of KRA-533 are shown.
Figure 2B:
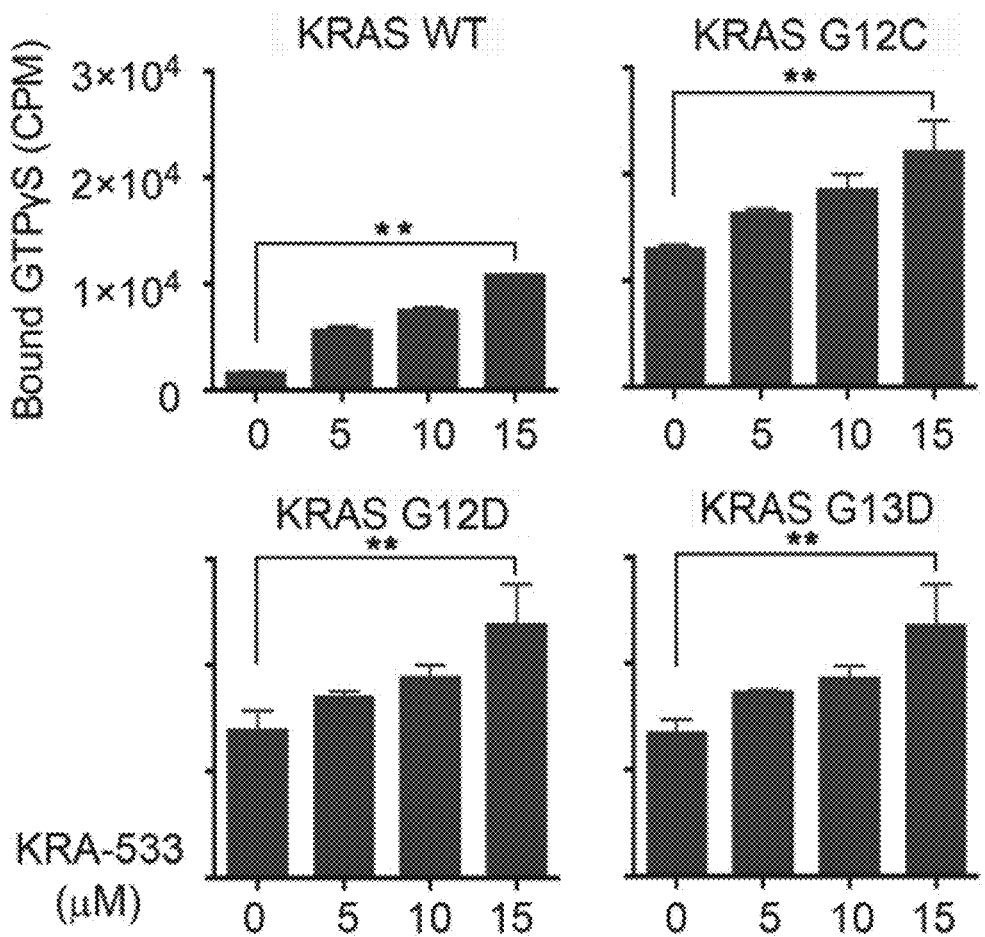
FIG. 2B shows data using 600 nM purified KRAS protein (WT, G12C, G12D or G13D) that was incubated with 11 µM [γ-35S] GTPγS, purified GFP (RASGRP1, 180 nM) and GAP (RASA1, 180 nM) at 25° C. in the presence or absence of increasing concentrations of KRA-533.
Figure 2C:
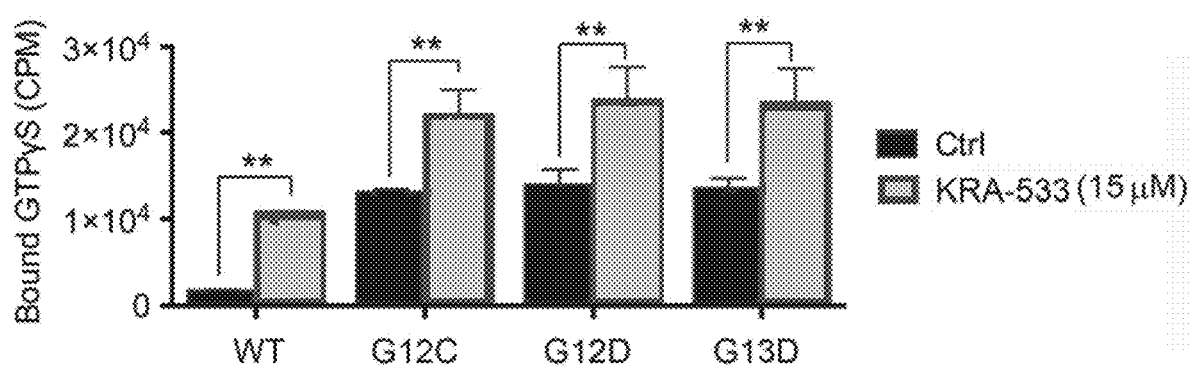
FIG. 2C shows the radioactivity remaining on the protein after intensive washing was quantified by liquid scintillation. This data indicates that KRA-533 directly binds to and activates KRAS in an in vitro cell-free system.

KRA-533 Directly Binds and Activates WT and Mutant KRAS in an In Vitro Cell-Free System To test whether KRA-533 directly binds to KRAS, a thermal shift assay was employed. Dose dependent increases in melting temperature (Tm) were observed when purified KRAS WT, G12C, G12D and G13D mutant proteins were incubated with increasing concentrations of KRA-533 (FIG. 2A). These results indicate that KRA-533 can directly bind to WT, G12C, G12D and G13D mutant KRAS proteins. To further assess whether KRA-533 activates KRAS directly, an in vitro cell-free GDP-GTP exchange experiment was carried out. Purified WT, G12C, G12D or G13D mutant KRAS proteins were incubated with purified GEF (RAS-GRP1) and GAP (RASA1) proteins in reaction buffer containing [γ-35S]-GTP in the absence or presence of increasing concentrations of KRA-533 at 25° C. for 60 min. KRAS activity was quantified by liquid scintillation counting. Mutant KRAS G12C, G12D and G13D displayed greater KRAS activity than WT KRAS in the absence of KRA-533 (FIG. 2B). Addition of KRA-533 activated WT KRAS to increase its activity in a dose-dependent manner. Intriguingly, KRA-533 further enhanced the activities of active KRAS mutants (i.e. G12C, G12D and G13D) (FIG. 2B). These findings indicate that KRA-533 not only activates WT KRAS but also has the capacity to further enhance KRAS activity of mutant KRAS.

K117 is a Required Site for KRA-533 to Bind and Activate KRAS

KRA-533 not only binds to but also directly activates WT and most common KRAS mutants, including G12C, G12D and G13D. Structural computational modeling analysis reveals that KRA-533 is associated with 15 amino acids (Leu120, Asn85, Phe28, Glu31, Asp30, Ala18, Pro34, Val29, Asp33, Lys117, Val14, Lys16, Asp57, Ser17 and Tyr32) in the GDP/GTP binding pocket. Among KRA-533-associated amino acids in the KRAS protein, two interactions are predicted with residues Ser17 and Lys117. These two sites were mutated to Ala individually or simultaneously, leading to generation of S17A, K117A and AA (i.e. S17A/K117A) KRAS mutants.

Figure 3A:
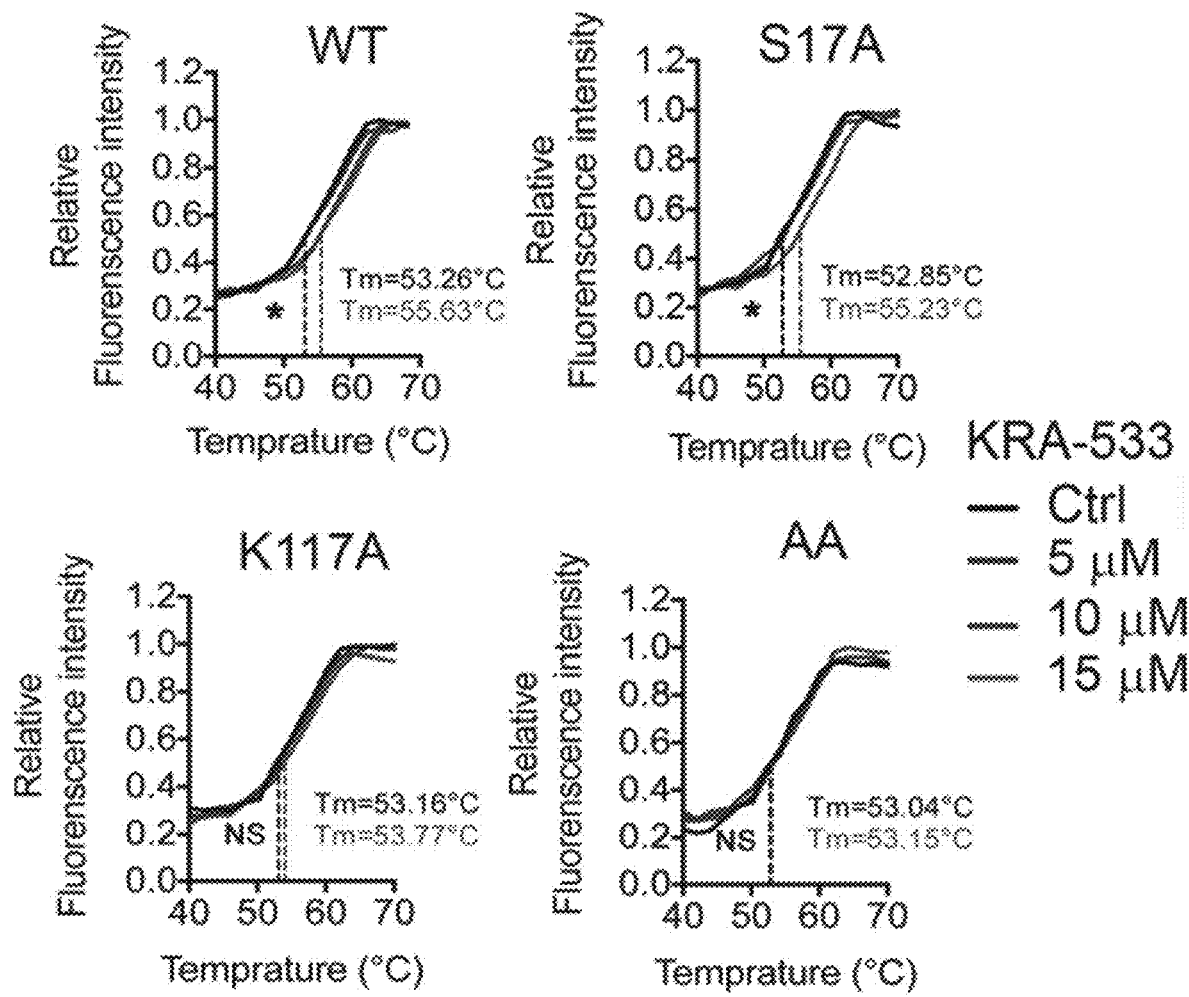
FIG. 3A shows thermal shift melting curves of purified KRAS protein (WT, S17A, K117A, or S17A/K117A (AA)) incubated with increasing concentrations of KRA-533. Melting temperature (Tm) values of DMSO control and 15 µM KRA-533 are shown.
Figure 3B:
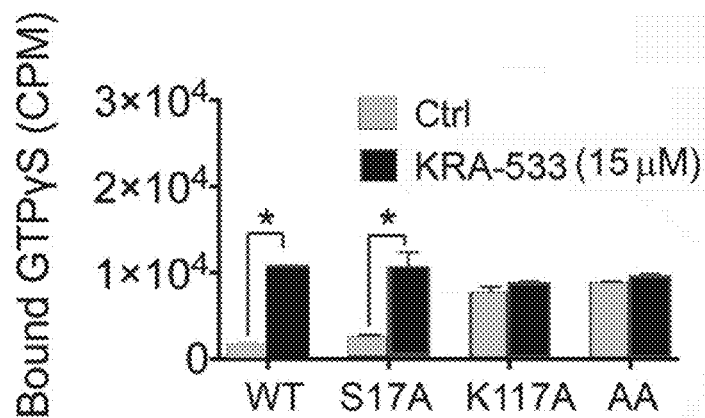
FIG. 3B shows data when 600 nM purified KRAS protein (WT, S17A, K117A or AA) was incubated with 11 µM [γ-35S] GTPγS, purified GFP (RASGRP1, 180 nM) and GAP (RASA1, 180 nM) at 25° C. in the presence or absence of 15 µM KRA-533. The radioactivity remaining on the protein after intensive washing was quantified by liquid scintillation.
Figure 3C:
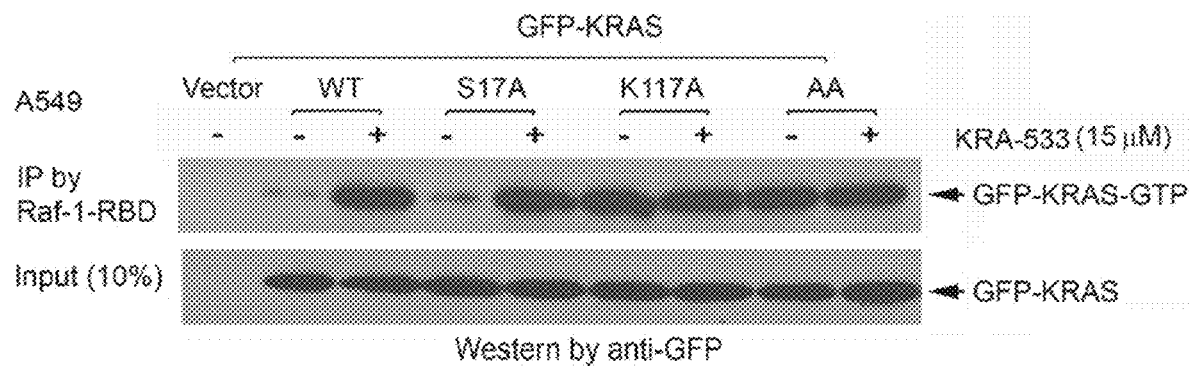
FIG. 3C shows data when A549 cells were transfected with GFP-tagged KRAS WT, S17A, K117A or AA, followed by treatment with KRA-533 (15 µM) for 48 h. KRAS GTP (active KRAS) was pulled down by Raf-1-RBD. The GFP-tagged exogenous KRAS-GTP (GFP-KRAS-GTP) was analyzed by Western blot using anti-GFP antibody. This data indicates that K117 site is important for KRA-533 to bind and activate KRAS.

Thermal shift assay indicates that KRA-533 could bind to recombinant WT and S17A KRAS proteins but failed to bind K117A and AA mutant KRAS proteins (FIG. 3A). Intriguingly, KRA-533 directly activated WT and S17A but not K117A mutant KRAS in a cell-free GDP-GTP exchange system (FIG. 3B). To further test this intracellularly, GFP-tagged WT, S17A, K117A and AA KRAS mutants were exogenously transfected into A549 cells. Then, cells were treated with KRA-533 for 48 h, followed by Raf-1-RBD beads pull-down. Activities of exogenous GFP-tagged WT and KRAS mutants were analyzed by Western blot using GFP antibody. Consistently, KRA-533 activated exogenous WT and S17A but not K117A KRAS mutant in A549 cells (FIG. 3C). These findings suggest that the Lys117 is required for KRA-533 to activate KRAS.

Figure 4A:
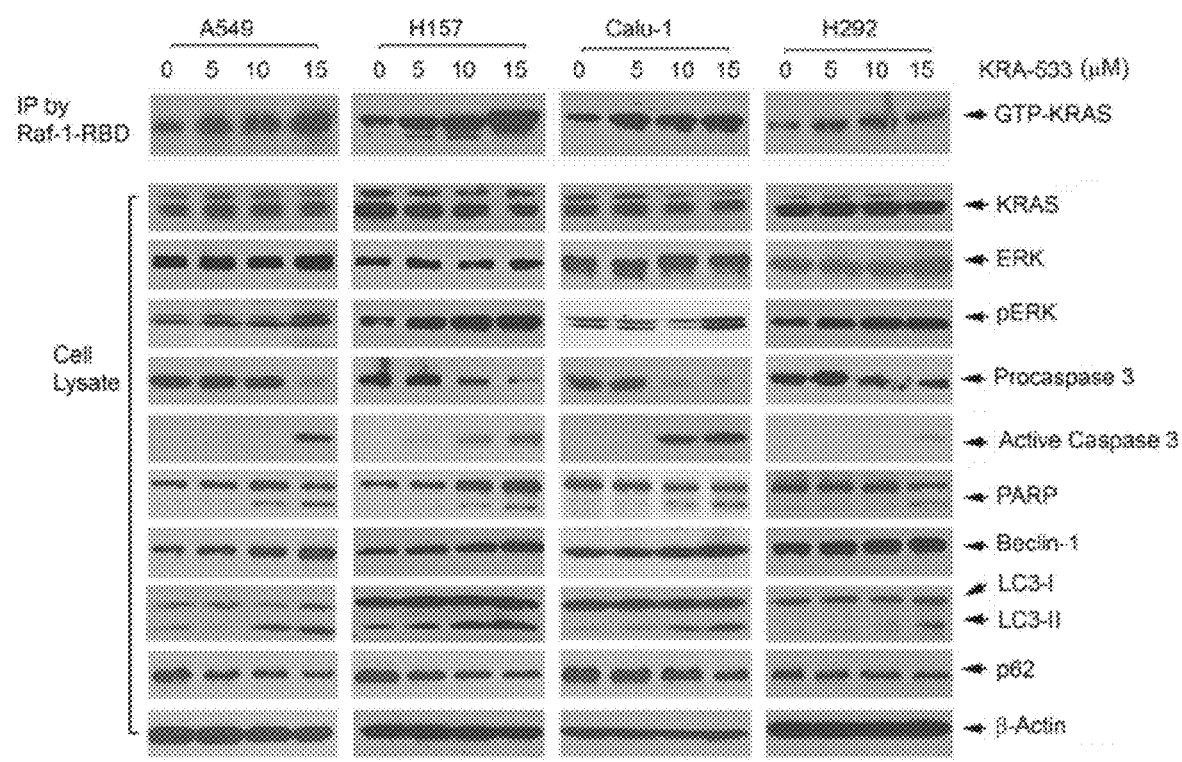
FIG. 4A shows data when A549, H157, Calu-1 and H292 cells were treated with increasing concentrations (0, 5, 10, 15 µM) of KRA-533 for 48 h. "0" means DMSO vehicle control. KRAS-GTP (active form of KRAS) was pulled down by Raf-1-RBD, followed by Western blot using KRAS antibody. Expression levels of KRAS, pERK, active caspase 3, PARP cleavage, Beclin1, LC3-I and LC3-II in total lysate were analyzed by Western blot.
Figure 4B:
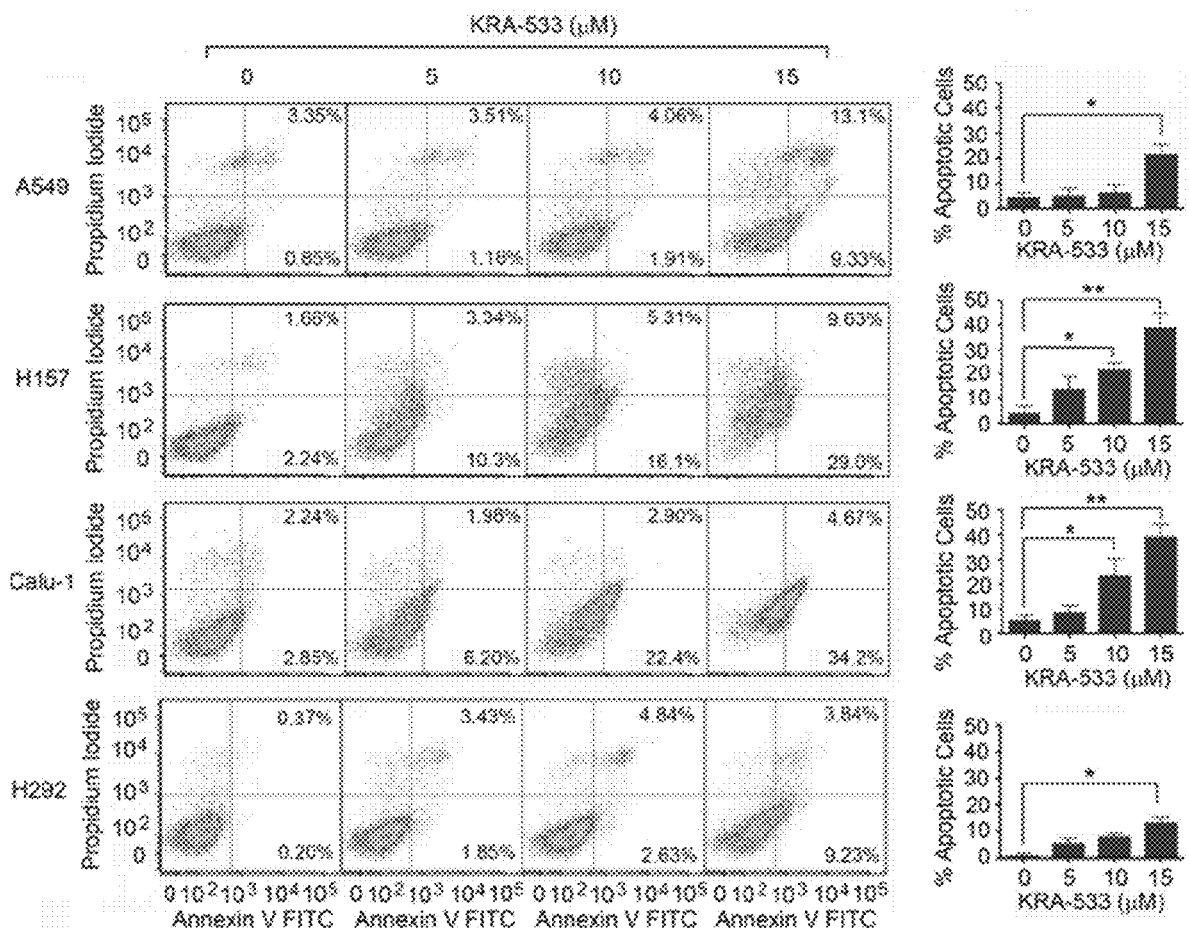
FIG. 4B shows data when apoptosis was determined by analyzing Annexin-V/PI binding by FACS.
Figure 4C:
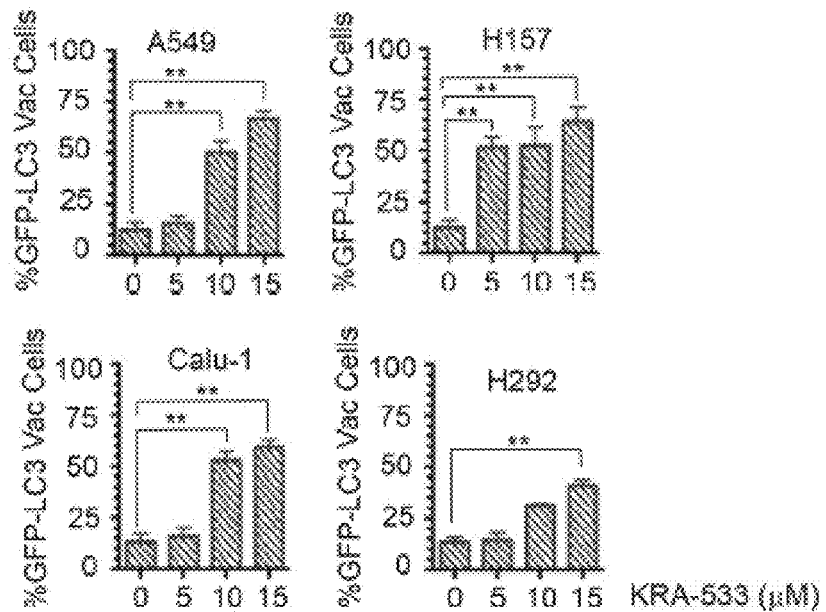
FIG. 4C shows data when GFP-LC3 plasmids were transfected into A549, H157, Calu-1 and H292 cells. After 24 h, cells were treated with KRA-533 for 48 h. The percentages of LC3-GFP-transfected cells bearing LC3-GFP aggregates (LC3-FGPvac) were quantified as shown. This data indicates KRA-533 induces KRAS activation leading to apoptotic and autophagic cell death in human lung cancer cells.

KRA-533-Induced KRAS Activation Promotes Apoptosis and Autophagic Cell Death in Human Lung Cancer Cells Activated KRAS can trigger cell death via apoptosis and autophagy-associated cell death in cancer cells. To test whether KRA-533-activated KRAS promotes apoptosis and autophagic cell death, A549, H157, Calu-1 and H292 cells were treated with increasing concentrations of KRA-533 for 48 h, followed by analysis of KRAS activity, apoptosis and autophagy. KRA-533 enhanced KRAS activity in a dose-dependent manner, which was associated increased levels of pERK, ratio of active caspase 3/procaspase 3 and PARP cleavage, leading to apoptotic cell death determined by FACS analysis of Annexin V/PI staining (FIGS. 4A and B), measurement of caspase 3 activity using a Caspase 3 Colorimetric Assay Kit and mitochondrial membrane potential using JC-1 staining. Autophagy was measured by analysis of LC3-I/LC3-II and p62 following treatment of cells with KRA-533. It is well known that p62 is an autophagy receptor or substrate that can be degraded by autophagy. In addition to LC3-II, p62 was analyzed as another autophagy marker. Intriguingly, KRA-533 induced a dose-dependent increase of LC3-II and a dose-dependent decrease of p62 in A549, H157, Calu-1 cells and H292 (FIG. 4A). To further quantify the level of autophagy, a GFP-LC3 construct was used to indicate autophagosomes. After treatment with KRA-533, GFP-LC3 redistributed from a diffuse staining pattern in the cytoplasm and nucleus to a cytoplasmic punctate structure that specifically labels pre-autophagosomal and autophagosomal membranes (i.e. GFP-LC3 vac cells). Intriguingly, KRA-533 enhanced the percentage of GFP-LC3vac cells in a dose-dependent manner (FIG. 4C). These findings indicate that, in addition to apoptosis, KRA-533 can also induce autophagic cell death. Importantly, A549, H157 and Calu-1 cells with KRAS mutation were significantly more sensitive than H292 cells without KRAS mutation to KRA-533-stimulated KRAS activation, induction of apoptosis and autophagy, suggesting that KRA-533 may be relatively selective for cancer cells bearing KRAS mutation(s).

To assess whether the autophagy inhibitor regulates KRA-533-induced autophagy formation, A549 and H157 cells were treated with KRA-533 in the absence or presence of autophagy inhibitor chloroquine for 48 h, followed by Western blot analysis of the autophagy marker p62. KRA-533 induced autophagy with deceased p62 level via degradation. The autophagy inhibitor chloroquine restored p62 expression by blocking KRA-533-induced p62 degradation. These findings indicate that autophagy inhibitor chloroquine has ability to block KRA-533-induced autophagy.

To determine whether autophagy plays a role in apoptosis induced by KRA-533, apoptosis was measured by FACS analysis of Annexin V/PI staining following treatments of A549 and H157 with KRA533 alone or in combination with autophagy inhibitor 3-MA for 48 h. Results indicate that the autophagy inhibitor 3-methyladenine (3-MA) enhanced KRA-533-induced apoptosis.

To further test whether KRAS is a required target for KRA-533 to induce apoptotic and autophagic cell death, G12S mutant KRAS was depleted using KRAS shRNA from A549 cells, followed by treatment with KRA-533 (15 μM) for 48 h. Knockdown of mutant KRAS significantly reduced cell sensitivity to the induction of apoptotic and autophagic cell death by KRA-533. Although embodiments of this disclosure are not limited by any particular mechanism, these findings suggest that KRAS may be a target for KRA-533 against lung cancer via apoptotic and autophagic cell death pathways.

KRA-533 Suppresses Mutant KRAS Lung Cancer in Xenograft Models

To define the appropriate doses of KRA-533 for in vivo experimentation, standard single-dose maximum tolerated dose (MTD) was determined. Nu/Nu nude mice were treated with a single dose of 150, 300 or 400 mg/kg i.p., followed by toxicity observations. Treatment of mice with a single dose of 150 or 300 mg/kg i.p. did not cause weight loss or other toxicities, including hematologic disorders, or liver and kidney function abnormalities. However, a single dose of 400 mg/kg resulted in death of mice in 8 days. Alanine transaminase (ALT), aspartate transaminase (AST) and blood urea nitrogen (BUN) were significantly elevated. Based on these findings, mice might die mainly from liver and kidney damage at a single 400 mg/kg dose. Thus, the single dose MTD of KRA-533 ranges from 300 to 400 mg/kg. One tenth of single-dose MTD was contemplated (~30-40 mg/kg) for continuous treatment, e.g., between 10 and 30 mg/kg/day.

Figure 5A:
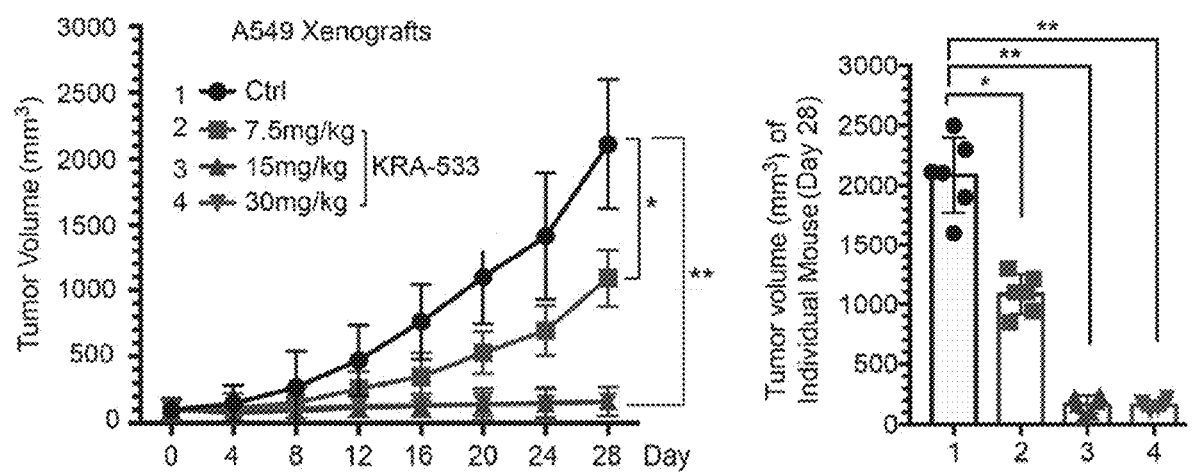
FIG. 5A shows data when Nu/Nu nude mice with A549 xenografts bearing mutant KRAS were treated with increasing doses of KRA-533 (0, 7.5, 15, and 30 mg/kg/d) for 28 days (n=6). Tumor volume was measured once every 2 days (left panel). Tumor volumes of 6 individual mice in each group were compared on day 28 (right panel). After 28 days, the mice were sacrificed, and the tumors were removed and analyzed.
Figure 5B:
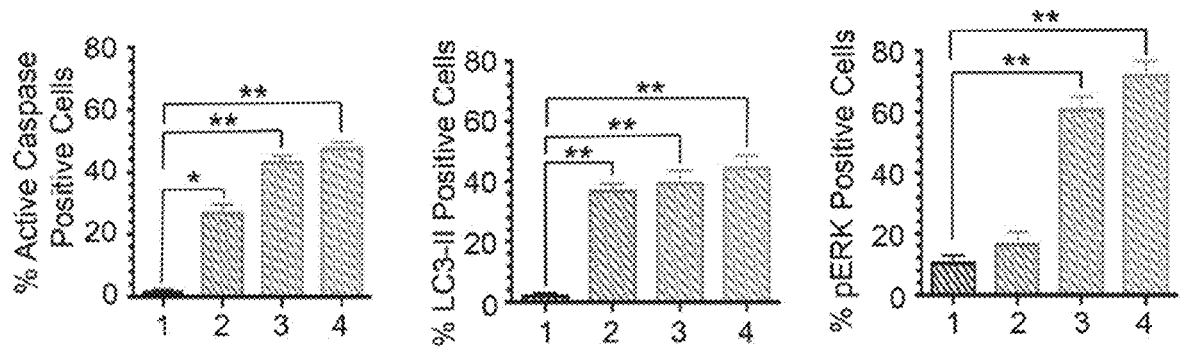
FIG. 5B shows data when active caspase-3, LC3-II and p-ERK were analyzed by IHC staining in tumor tissues at the end of experiments and quantified.
Figure 5C:
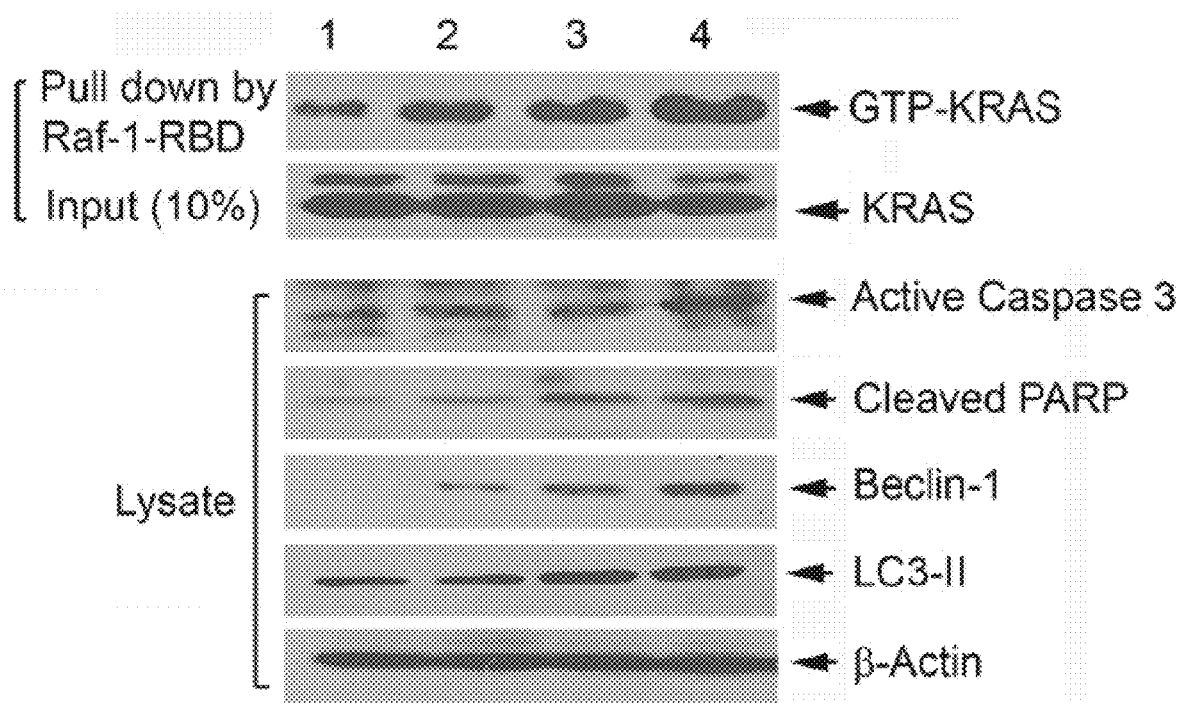
FIG. 5C shows data when KRAS-GTP (active form of KRAS) was pulled down by Raf-1-RBD from tumor tissue lysates, followed by Western blot using KRAS antibody. Expression levels of active caspase-3, cleaved PARP, Beclin-1 and LC3-II in tumor tissues were analyzed by Western blot. This data indicates KRA-533 suppresses tumor growth in KRAS mutant lung cancer xenografts.

To test the potency of KRA-533 in vivo, lung cancer xenografts derived from A549 cells bearing KRAS mutation (G12S) were treated with increasing doses (0, 7.5, 15, and 30 mg/kg/day) of KRA-533 i.p. for 28 days. KRA-533 suppressed tumor growth in a dose-dependent manner in lung cancer mutant KRAS xenografts (FIG. 5A). To assess whether KRA-533 induced suppression of tumor growth via apoptosis and autophagy in vivo, representative samples from harvested tumor tissues were analyzed by immunohistochemistry (IHC) for active caspase-3 or LC3-II. Indeed, KRA-533 induced apoptosis and autophagy in tumor tissues in a dose-dependent manner (FIG. 5B). Raf-1-RBD pull-down experiments for KRAS activity were also carried out using total cell lysates isolated from tumor tissues. Treatment of mice with KRA-533 resulted in accumulation of active KRAS in tumor tissues in association with increased apoptosis and autophagy (FIG. 5C), suggesting KRA-533-mediated tumor suppression may occur through induction of apoptosis and autophagic cell death. Treatment was well tolerated without significant toxicity within effective dose range (7.5 30 mg/kg/d). There was no weight loss. Tests of blood cells (WBC, RBC and PLT) for bone marrow, BUN for kidney and ALT/AST for liver functions were in the normal range. Histopathology of harvested normal tissues (brain, heart, lung, liver, spleen, kidney and intestine) revealed no evidence of normal tissue toxicities after treatment with doses of 7.530 mg/kg/day. These findings suggest that doses between 7.5 and 30 mg/kg provide the optimal therapeutic index for KRA-533 for in vivo studies.

KRA-533 Potently Inhibits Tumor Growth and Prolongs Survival of Mice with Genetically Engineered G12D Mutant KRAS-Driven Lung Cancer KRAS mutations are common genetic alterations in NSCLC and contribute to the resistance of lung cancer to conventional therapy. To test the potency of KRA-533 in mutant KRAS-driven lung cancer, lox-stop-lox (LSL)-KRASG12D mice were generated. By engineering LoxP DNA elements into the mouse genome that surround a synthetic 'stop' element (lox-stop-lox) inserted in front of mutant KRAS G12D, one can 'turn-on' mutant KRAS G12D with delivery of Cre recombinase. To control the expression of KRAS G12D, a LSL cassette was engineered into the first intron of the KRAS gene. The LSL cassette consists of transcriptional and translational stop elements flanked by LoxP sites that prevent the expression of the mutant allele until the stop elements are removed by the activity of Cre recombinase. To produce KRAS G12D mutant-driven lung cancer, alleles were induced in mouse lung using intranasal administration of a lentiviral Cre recombinase. Primary lung tumors developed around 12 weeks post-inoculation.

To assess whether KRA-533 has antitumor activity against G12D mutant KRAS-driven lung cancer in genetically engineered mouse models, KRA-533 (20 mg/kg/d) or vehicle control was administered i.p. starting at 10 weeks post AdeCre delivery. After treatment for 3 months, mice were euthanized for analysis of tumor burden. Treatment of KRAS G12D mice with KRA-533 for four months resulted in significant reduction of tumor burden and multiplicity in the lung (FIG. 7A). Importantly, KRA-533 prolonged survival of KRAS G12D mice compared with the control group (FIG. 7B). There were 3 deaths out of 8 mice in the control group versus 1 death out of 8 mice in the KRA-533 treatment group in four months before euthanization. Slight weight loss but no significant normal tissue toxicitie were observed in mice.

KRA-533 in Genetically Engineered LSL-KRASG12D LKB1fl/fl (KL) Mice

Figure 6A:
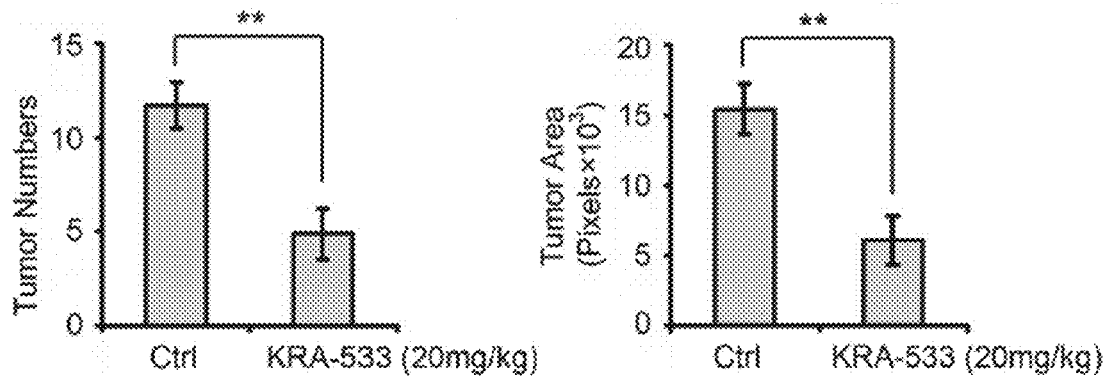
FIG. 6A shows data when after administration of adenovirus Cre recombinase in KRASG12D mice for 10 weeks, mice were treated with KRA-533 (20 mg/kg/d) for four months (n=8 each group). Tumor numbers were counted under the microscope and tumor area was quantified using modular imaging software.
Figure 6B:
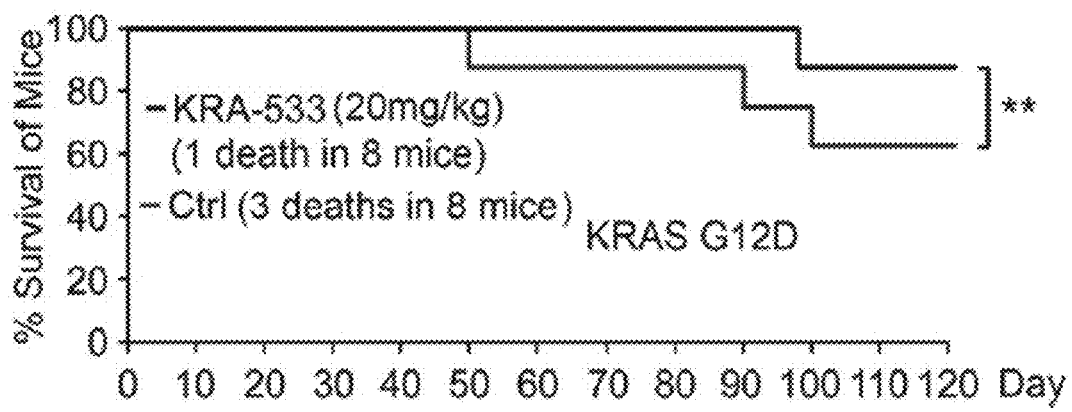
FIG. 6B shows survival data of mice four months before euthanization in the control group versus the KRA-533 treatment group. This data indicates KRA-533 inhibits mutant KRASG12D driven lung cancer growth in genetically engineered mouse model.
Figure 6C:
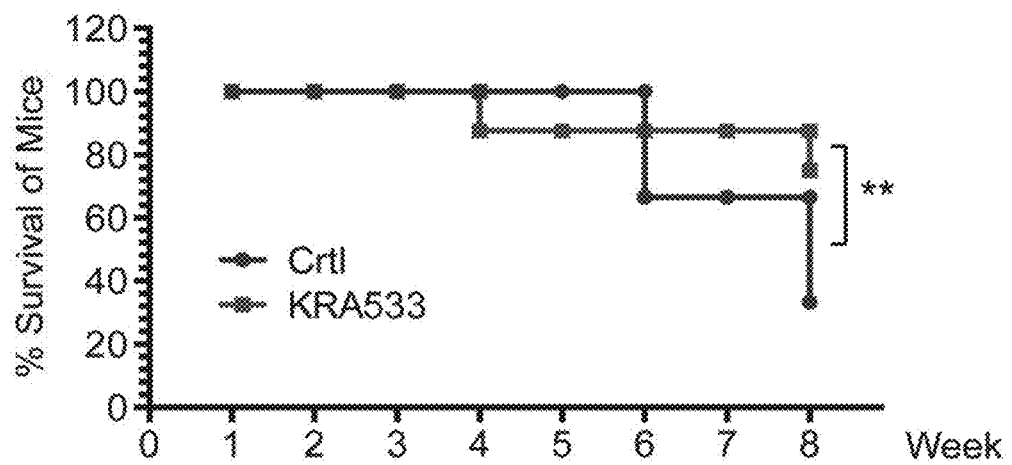
FIG. 6C shows when KRA-533 was administered to genetically engineered LSL-KRASG12D LKB1fl/fl (KL) mice. After administration of adenovirus Cre recombinase in KL mice for 6 weeks, mice were treated with KRA-533 (20 mg/kg/d) for 8 weeks (n=6 each group). Survival of mice was calculated up to 8 weeks before euthanization in the control group versus the KRA-533 treatment group.

It is reported that the co-occurrence of KRAS and LKB1 (STK11) mutations could label a more aggressive molecular subtype of NSCLC. Around half of KRAS-mutant lung cancer patients also carry LKB1 mutations, therefore, it will be important to test whether KRA-533 is also effective for the treatment of KRAS-mutant lung cancers with mutation or loss. LSL-KRASG12D LKB1fl/fl (KL) mice were generated by intercrossing B6.129S4-Krastm3Tyj/J (KRASG12D) and FVB; 129S6-Stk11tm1Rdp/Nci (LKB1) strains two generations and genotyped to confirm homozygosity for the LKB1 allele. These mice contain a KRASG12D LSL knock-in allele and a floxed allele of LKB1 (LKB1fl/fl). KRA-533 (20 mg/kg/d) or vehicle control was administered i.p. starting at 6 weeks post AdeCre delivery. After treatment for 8 weeks, mice were euthanized, and lung tumors were analyzed as described above. Results reveal that KRA-533 also significantly suppressed tumor growth and prolonged survival of KL mice (FIG. 6C).

What is claimed is:

1. A method of treating cancer comprising administering an effective amount of 4-(4-(2-bromoacetamido)butyl)benzoic acid, prodrug, or salt thereof to a subject thereof.

2. The method of claim 1, wherein the subject is diagnosed with multiple myeloma, leukemia, lymphoma, lung, pancreatic, colorectal, uterine, esophageal, gastric, cervical, or bladder cancer.

3. The method of claim 1, wherein an effective amount is between 7.5 and 30 mg/kg/day.

4. The method of claim 1, wherein the subject is diagnosed with a KRAS mutation.

5. The method of claim 1, wherein the subject is diagnosed with a glycine to cysteine mutation at position 12, a glycine to aspartic acid at position 12, a glycine to arginine at position 12, a glycine to serine at position 12, a glycine to valine at position 12, or a glycine to aspartic acid at position 13, a glutamine to histidine at position 61, an alanine to threonine at position 146, or combinations thereof.

6. The method of claim 1, wherein the subject is diagnosed with a nonmutated lysine (K) in KRAS at amino acid position 117.

7. The method of claim 4, wherein the subject is diagnosed with an LKB1 inactivating mutation.

8. The method of claim 1, wherein 4-(4-(2-bromoacetamido)butyl)benzoic acid, prodrug, or salt thereof is administered in combination with an additional chemotherapy agent.

* * * * *